US008367891B2

(12) United States Patent
Yin et al.

(10) Patent No.: US 8,367,891 B2
(45) Date of Patent: Feb. 5, 2013

(54) N-TERMINAL XA27 SIGNAL ANCHOR AND ITS USE FOR LOCALIZATION OF FUSION PROTEINS

(75) Inventors: Zhongchao Yin, Singapore (SG); Lifang Wu, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 241 days.

(21) Appl. No.: 12/742,170

(22) PCT Filed: Nov. 15, 2007

(86) PCT No.: PCT/SG2007/000394
§ 371 (c)(1),
(2), (4) Date: May 10, 2010

(87) PCT Pub. No.: WO2009/064255
PCT Pub. Date: May 22, 2009

(65) Prior Publication Data
US 2010/0299787 A1    Nov. 25, 2010

(51) Int. Cl.
*C12N 15/82* (2006.01)
*C07H 21/04* (2006.01)

(52) U.S. Cl. ....... 800/278; 435/468; 435/419; 536/23.4; 536/23.6

(58) Field of Classification Search .................... None
See application file for complete search history.

(56) References Cited

U.S. PATENT DOCUMENTS

| | | | |
|---|---|---|---|
| 7,351,817 B2 * | 4/2008 | Yin et al. | 536/23.6 |
| 2004/0123343 A1 | 6/2004 | La Rosa et al. | |
| 2006/0143734 A1 | 6/2006 | Yin et al. | |
| 2010/0162438 A1 * | 6/2010 | Yin et al. | 800/279 |

OTHER PUBLICATIONS

Gu et al. R gene expression induced by a type-III effector triggers disease resistance in rice. (2005) Nature; vol. 435; pp. 1122-1125.*
Gu et al. Oryza sativa (indica cultivar-group) Xa27 (Xa27) mRNA, Xa27-IRBB27 allele, complete cds. (2005) GenBank Accession AY986493; pp. 1-2.*
Database NCBI GenBank, Gu et al., Oryza sativa (indica cultivar-group) xa27 (xa27) gene, xa27-IR24 allele, complete cds, Jun. 24, 2005., NCBI/GenBank Acc. No. AY986491. Sequence shares 100% identity with SEQ ID No. 1 between nucleotides 1590-1931.
Database NCBI GenBank, Gu et al., Oryza sativa (indica cultivar-group) xa27 (xa27) gene, Xa27-IRBB27 allele, complete cds, Jun. 24, 2005, NCBI/GenBank Acc. No. AY986492, Sequence shares 100% identity with SEQ ID No. 1 between nucleotides 1558:1899. Sequence shares 100% identity with SEQ ID No. 1 between nucleotides 1558-1899.
Database NCBI GenBank, Gu et al., Oryza sativa (indica cultivar-group), Xa27-IRBB27 (xa27) gene, mRNA, Xa27-IRBB27 allele, complete cds, Jun. 24, 2005, NCBI/GenBank Acc. No. AY986493, Sequence shares 100% identity with SEQ ID No. 1 between nucleotides 61-402. Sequence shares 100% identity with SEQ ID No. 1 between nucleotides 61-402.
Gu et al., "R gene expressions induced by a type-III effector triggers disease resistance in rice," Nature Letters, Jun. 23, 2005, vol. 435, pp. 1122-1125.
Database NCBI GenBank, Sasaki et al., Oryza sativa (japonica cultivar-group) genomic DNA, chromosome 6, PAC clone: P0642B07, Feb. 16, 2008, NCBI/GenBank Acc. No. AP003623. See sequence between nucleotides 105246-105413.
Database NCBI GenBank, Sasaki et al., Oryza sativa (japonica cultivar-group) genomic DNA, chromosome 6, BAC clone: OSJNBa0033B09, Feb. 16, 2008. NCBI/GenBank Acc. No. AP002864. See sequence between nucleotides 41566-41733.
Database NCBI GenBank, Sasaki et al., Oryza sativa (japonica cultivar-group) genomic DNA, chromosome 6, clone P068A03, Feb. 15, 2008. NCBI/GenBank Acc. No. AB023482. See sequence between nucleotides 116416-116583.
Xing, Haoran, "Subcellular Localization of XA21 and Identification of Key Localized Domain," China Master's Theses Full-Text Database (e-Journal), Agricultural Science Volume, 2006 (8), 3 pages.

* cited by examiner

*Primary Examiner* — Cathy Kingdon Worley
(74) *Attorney, Agent, or Firm* — Rothwell, Figg, Ernst & Manbeck pc

(57) ABSTRACT

The present application is directed to a functional signal anchor that localizes a fusion protein to the apoplast of vascular elements in plants. The signal anchor is useful for engineering secretory proteins to the cell wall and or/apoplast of plant cells. The signal anchor is also useful for producing secretory proteins in transgenic plant cells in a bioreactor.

14 Claims, 7 Drawing Sheets

SEQUENCE LISTING

```
<160> NUMBER OF SEQ ID NOS: 4

<210> SEQ ID NO 1
<211> LENGTH: 171
<212> TYPE: DNA
<213> ORGANISM: Oryza sativa
<220> FEATURE:
<221> NAME/KEY: CDS
<222> LOCATION: (1)..(171)

<400> SEQUENCE: 1 atg gcg gat tgg gcg atg cac cac tac ctc cta cta gcc aac cag caa      48
Met Ala Asp Trp Ala Met His His Tyr Leu Leu Leu Ala Asn Gln Gln
1               5                   10                  15 cgc cac cga gcc ctc gcc gac gtc gcc gtc cgc cgc cgc cag ctg ctc      96
Arg His Arg Ala Leu Ala Asp Val Ala Val Arg Arg Arg Gln Leu Leu
            20                  25                  30 ctc gac tcc ggc cgc gtc ttc atg ctc ctc ggc gcc gtc atc ctc atg     144
```

```
Leu Asp Ser Gly Arg Val Phe Met Leu Leu Gly Ala Val Ile Leu Met
        35                  40                  45 cac atg ctc acc act acc ggc ggc gga                              171
His Met Leu Thr Thr Thr Gly Gly Gly
    50                  55

<210> SEQ ID NO 2
<211> LENGTH: 57
<212> TYPE: PRT
<213> ORGANISM: Oryza sativa

<400> SEQUENCE: 2

Met Ala Asp Trp Ala Met His His Tyr Leu Leu Leu Ala Asn Gln Gln
1               5                   10                  15

Arg His Arg Ala Leu Ala Asp Val Ala Val Arg Arg Arg Gln Leu Leu
            20                  25                  30

Leu Asp Ser Gly Arg Val Phe Met Leu Leu Gly Ala Val Ile Leu Met
        35                  40                  45

His Met Leu Thr Thr Thr Gly Gly Gly
    50                  55

<210> SEQ ID NO 3
<211> LENGTH: 70
<212> TYPE: PRT
<213> ORGANISM: Oryza sativa

<400> SEQUENCE: 3

Met Ala Asp Trp Ala Met His His Tyr Leu Leu Leu Ala Asn Gln Gln
1               5                   10                  15

Arg His Arg Ala Leu Ala Asp Val Ala Val Arg Arg Arg Gln Leu Leu
            20                  25                  30

Leu Asp Ser Gly Arg Val Phe Met Leu Leu Gly Ala Val Ile Leu Met
        35                  40                  45

His Met Leu Thr Thr Thr Gly Gly Gly Ala Ser Ser Gly Cys Thr Arg
    50                  55                  60

Gly Ala Glu Pro Cys Val
65                  70

<210> SEQ ID NO 4
<211> LENGTH: 9
<212> TYPE: RNA
<213> ORGANISM: Oryza sativa
<220> FEATURE:
<221> NAME/KEY: misc_feature
<222> LOCATION: (2)..(5)
<223> OTHER INFORMATION: n is a, c, g, or u

<400> SEQUENCE: 4 annnnaugg                                                          9
```

N-TERMINAL XA27 SIGNAL ANCHOR AND ITS USE FOR LOCALIZATION OF FUSION PROTEINS

CROSS-REFERENCE TO RELATED APPLICATIONS

Figure 1:
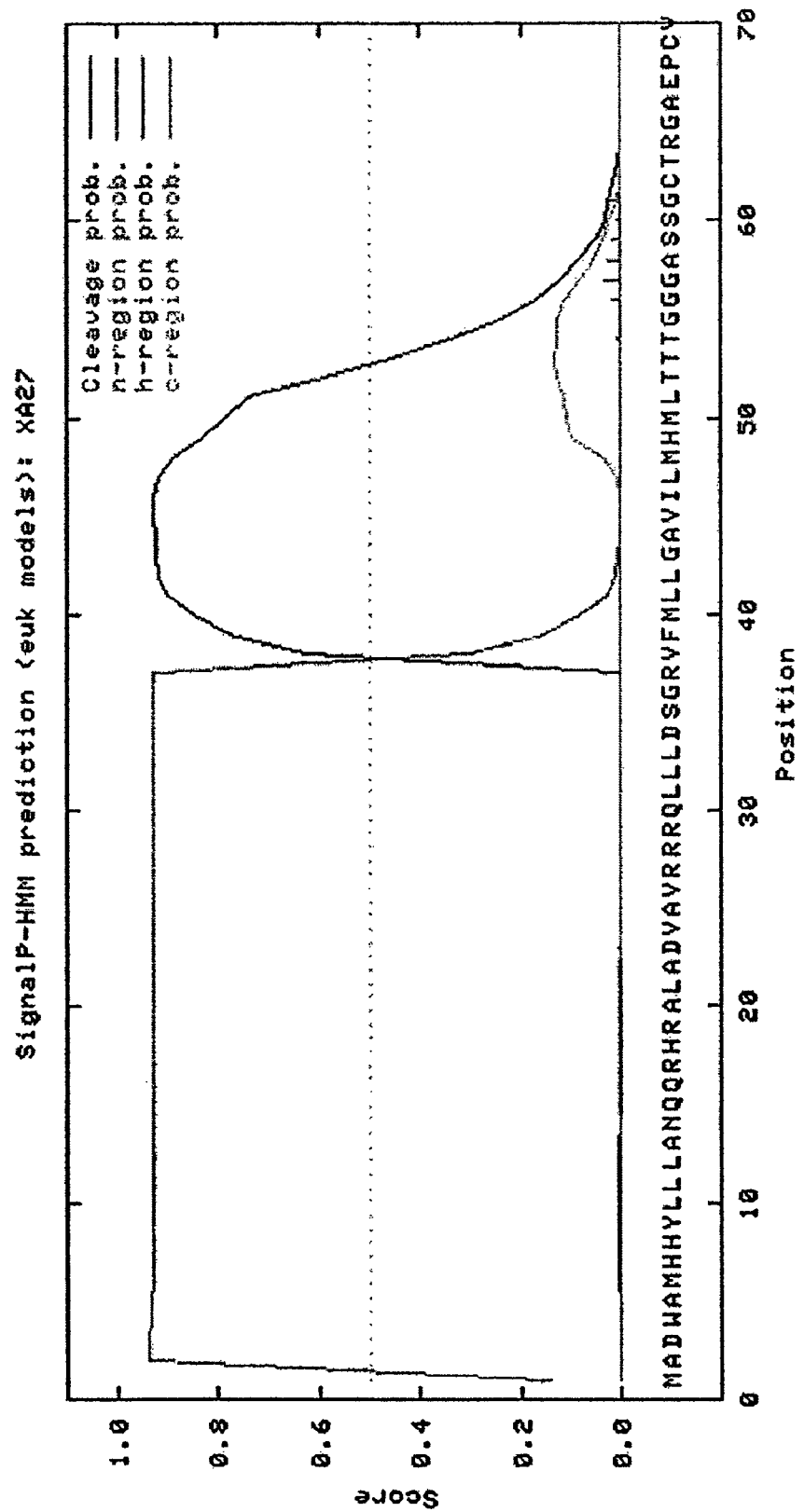

The present application is a national stage filing under 35 U.S.C. §371 of PCT/SG2007/000394, filed on 15 Nov. 2007, the disclosure of which is incorporated herein by reference.

SEQUENCE SUBMISSION

The present application includes a Sequence Listing filed in electronic format. The Sequence Listing is entitled 2577183SequenceListingR.txt, was created on 6 Sep. 2012 and is 3 kb in size. The information in the electronic format of the Sequence Listing is part of the present application and is incorporated herein by reference in its entirety.

BACKGROUND OF THE INVENTION

The present invention is directed to a functional signal anchor that localizes a fusion protein to the apoplast of vascular elements in plants. The signal anchor is useful for engineering secretory proteins to the cell wall and/or apoplast of plant cells. The signal anchor is also useful for producing secretory proteins in transgenic plant cells in a bioreactor.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Xylem and phloem of plant vascular system are major conduits for transportation of water and solutes through the plant (Canny, 1986; Kim and Guerinot, 2007). Xylem and phloem are targets of various kinds of plant pathogens, such as bacteria, fungi and insects. A number of phloem-feeding insects, such as aphids and planthoppers, are highly destructive agricultural pests worldwide (Backus et al 2004, Moran et al, 2001). These pests mainly feed on the stems and suck in the phloem sieve elements, thus, causing direct feeding damage to the crop (e.g. hopper bum) (Moran et al, 2001). These pests also transmit viral diseases that cause additional damages (Noda et al, 1991). Though spraying poisonous chemicals is the usual means used in pest control, which is laborious, expensive and more over not environment-friendly, therefore, use of other safe and economic alternatives of pest control are needed. A number of plant or bacterium derived toxin proteins having insecticidal properties are available and used in transgenic crops (Carlini and Grossi-de-Sa, 2002, Chattopadhyay et al., 2004). The adoption of insect-resistant transgenic crops has been increasing annually ever since the commercial release of the first-generation maize and cotton expressing a single modified *Bacillus thuringiensis* toxin (Bt) (Christou et al., 2006).

These toxin proteins act differentially against different classes of insects and the toxicity of most of plant derived toxins and Bt to aphids and planthoppers are either unknown or with no effect (Carlini and Grossi-de-Sa, 2002). This is partially due to the fact that the two kinds of insect are phloem-feeding insects, whereas the toxin proteins localize to cytoplasm of plant cell. Similarly, the engineered proteins need to be secreted to plant culture media when transgenic plant cells are used as a natural bioreactor (James and Lee, 2001). In either of the cases, efficient secretion of the engineered proteins to apoplast of plant cells should be considered.

Plants do allow the cost-effective production of recombinant proteins on an agricultural scale, while eliminating risks of product contamination with endotoxins or human pathogens (Fischer and Emans, 2000; Giddings et al., 2000; Ma et al., 2003; Twyman et al., 2003). Plant suspension cells can be employed as host cells for the production of foreign proteins. The main advantages of using transgenic plant cells are due to the fact that the plant culture media is inexpensive and simple. The mammalian proteins produced from plant cells were found to be correctly glycosylated and secreted into the medium (James and Lee, 2001).

Plant disease resistance (R) genes confer race-specific resistance to pathogens that have cognate avirulence (avr) genes (Flor, 1971). The R protein presumably functions as part of a receptor complex that recognizes an elicitor, which is directly or indirectly encoded by the cognate avr gene in the pathogen, and subsequently initiates defense responses (Hammond-Kosack and Jones, 1997; Martin et al., 2003). In recent years, extensive molecular and genetic analyses have been performed in a number of R-Avr systems. The majority of R proteins fall into five classes based primarily upon their combination of a limited number of structural motifs while a few other R proteins have novel structures or confers resistance to plant pathogens in a non-race-specific way (Dangl and Jones, 2001; Martin et al., 2003).

One of the interesting aspects of R protein function is its localization. R proteins have been found in a variety of cellular locations. The available information suggests that R proteins in general colocalize with pathogen effectors, indicating a clear display of spatial interdependency of both components (Martin et al., 2003). The direct physical interactions of R and Avr proteins have been demonstrated in several R-Avr pairs (Jia et al., 2000; Kim et al., 2002; Leister and Katagiri, 2000; Scofield et al., 1996; Tang et al., 1996). Viral effectors are present inside the plant cell, and the predicted structures of all known R proteins against viruses indicate that they are also intracellular (Burch-Smith et al, 2007). The tomato Cf proteins, which recognize extra-cellular *Cladosporium fulvum* Avr proteins (Lauge and De Wit, 1998), are localized to the plasma membrane (Rivas and Thomas, 2005). Fungal pathogen-directed R proteins can also be intracellular as fungal Avr proteins are delivered to and function inside plant cells (Jia et al., 2000).

All bacteria-directed R proteins are predicted to be intracellular, except XA21. This prediction is based on the fact that most of the bacterial Avr gene products are effector proteins, which are secreted to host cells through the bacterial type III secretion system (TTSS) (He et al., 2004). In fact, many R proteins do not carry recognizable subcellular targeting signatures and their localization needs to be determined experimentally. For instance, *Arabidopsis* RPM1 and RPS2 are associated with cellular membranes although they do not possess any canonical membrane targeting domains (Axtell and Staskawicz, 2003; Boyes et al., 1998). This subcellular localization is consistent with the membrane localization of their corresponding Avr elicitors, AvrRpm1 and AvrRpt2, respectively (Axtell and Staskawicz, 2003; Nimchuk et al., 2000). Apart from the plasma membrane, *Arabidopsis* RRS1-R and its cognate Avr protein PopP2 colocalize in the nucleus and the nuclear localization of RRS1-R is dependent on the presence of PopP2 (Deslandes et al., 2003). Recently, both tobacco N and barley MLA10 were found to localize to cytoplasm and nucleus, and nuclear retention of either R protein is indispensable for downstream signaling and defense (Burch-Smith et al., 2007; Shen et al., 2007). In these three cases, translocation of the R proteins during signaling might take place as well upon activation of the R proteins by the cognate Avr proteins (Burch-Smith et al., 2007; Deslandes et al., 2003; Shen et al., 2007). Rice XA21 is a transmembrane receptor kinase that presumably recognizes elicitor localized to apoplast of rice cells with its extracellular LRR portion (Song et al., 1995). The AvrXa21 molecule(s) corresponding to Xa21 has not yet been identified, although it appears that it might be a sulphated protein secreted to the apoplast through a type II secretion system and involved in quorum sensing (Lee et al., 2006).

The apoplast is the extraprotoplastic matrix of plant cells, consisting of all compartments from the external face of the plasmalemma to the cell wall (Dietz, 1997). The apoplast is important for all the plant's communication to its environment and plays an important role in signaling and defense upon pathogen attack (Dietz, 1997; Huckelhoven, 2007). Many extracellular enzymes and proteins located in apoplast or associated with cell wall are involved in signaling for defense or have antimicrobial function (Edreva, 2005; Huckelhoven, 2007). For example, the apoplast contains several low-molecular-weight and protein antioxidants, which control levels of reactive oxygen species (ROS) (Noctor et al., 2002; Pignocchi and Foyer 2003). Apoplastic levels and redox status of ascorbate and glutathione change during compatible and incompatible interactions of barley with *B. graminis* and several extracellular antioxidative enzyme activities also increase upon *B. graminis* attack (Noctor et al., 2002; Vanacker et al., 1998, 2000). The increase of peroxidase activity in extracellular space and accumulation of cationic peroxidase in xylem vessels was also detected during interaction of rice with *X. oryzae* pv *oryzae*, especially with incompatible interaction (Hilaire et al., 2001; Reimers et al., 1992. Young et al., 1995). Another group of proteins that are secreted to cell wall are pathogenesis-related (PR) proteins. The PR proteins include PR-1, chitinase, glucanases, proteases, thionins, osmotins, defensins, and some of them are only small peptides (Edreva, 2005; Huckelhoven, 2007). These PR proteins induced in resistant or systemic acquired resistance (SAR)-expressing plants, as well as from transgenic resistant plants exhibit high antimicrobial activity (Edreva, 2005). Most of the PR proteins are also induced by many environmental and developmental stimuli (Edreva, 2005).

Bacterial blight of rice, caused by *Xanthomonas oryzae* pv. *oryzae*, is one of the most destructive bacterial diseases of rice (Mew 1987). We previously reported isolation of resistance gene Xa27 from rice (Gu et al., 2005). Unlike other cloned R genes, Xa27-mediated resistance specificity to bacterial blight is determined by its promoter rather than by its gene product. Xa27-dependent resistance is associated with the specific induction of the R gene by incompatible pathogens harboring avrXa27. Ectopic expression of Xa27 coding region under rice PR1 promoter resulted in non-specific resistance to both incompatible and compatible strains. The Xa27 protein (XA27) has no sequence similarity with any previously characterized R-gene products.

There is a need to identify elements that are useful for localizing fusion proteins to specific locations within a plant or plant cell.

SUMMARY OF THE INVENTION

The present invention is directed to a functional signal anchor that localizes a fusion protein to the apoplast of vascular elements in plants. The signal anchor is useful for engineering secretory proteins or other proteins to the cell wall and/or apoplast of plant cells. The signal anchor is also useful for producing secretory proteins in transgenic plant cells in a bioreactor.

In one aspect, the present invention provides a nucleic acid molecule is provided that comprises a nucleotide sequence encoding a signal anchor. In one embodiment, the signal anchor is the XA27 signal anchor having SEQ ID NO:2. In another embodiment the nucleotide sequence encoding the XA27 signal anchor has the sequence set forth in SEQ ID NO:1. In a further embodiment, the nucleotide sequence is one which incorporates the degeneracy of the genetic code. In another embodiment, the nucleotide sequence is one which has been modified to contain plant preferred codons. In one embodiment, the signal anchor is a variant of the XA27 signal anchor. In another embodiment, the variant is the XA27 signal anchor having amino acid substitutions. Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired activity, i.e., signal anchor activity.

In a second aspect, the present invention provides a cassette containing the signal anchor encoding nucleotide sequence. In one embodiment, a cassette is provided with a plurality of restriction sites for insertion of coding sequence of a protein of interest to be linked to the signal anchor coding sequence to create a coding sequence for a fusion protein comprising the signal anchor and the protein of interest. In another embodiment, a cassette is provided which comprises a coding sequence for the signal anchor fused in proper reading frame to a coding sequence for the protein of interest to create the coding sequence for a fusion protein. The coding sequence for this fusion protein is sometimes referred to herein as a fusion gene. In a further embodiment, a cassette may also include regulatory regions operatively linked to the 5' side of the signal anchor encoding nucleotide sequence and/or to the 3' side of the restriction sites and hence to the 3' side of the inserted coding sequence for the protein of interest. A cassette containing all of these elements is also referred to herein as an expression cassette. In one embodiment, an expression cassette may additionally contain 5' leader sequences in the expression cassette construct. In another embodiment, an expression cassette may additionally contain selectable marker genes.

In a third aspect, the present invention provides transformed plants, plant cells, plant tissues and seeds thereof. In one embodiment, the cells that have been transformed may be grown into plants in accordance with conventional ways. In another embodiment, these plants may then be grown, and either pollinated with the same transformed strain or different strains, and the resulting hybrid having constitutive expression of the desired phenotypic characteristic identified. In a further embodiment, transformed plant cells are grown in culture to produce the protein of interest as a fusion protein which is purified and treated to obtain the protein of interest.

BRIEF DESCRIPTION OF THE FIGURES

FIG. 1 shows output of signalP-HMM prediction of XA27 (SEQ ID NO:3) from SignalP 3.0 server. A putative signal anchor was predicted to contain N-terminal positively charged n-region (residue 1-37) followed by a hydrophobic h-region (Emanuelsson et al., 2007). Full-length amino acid (aa) sequence of XA27 was submitted to SignalP 3.0 server (http: slash slash www dot cbs dot dtu dot dk slash services slash SignalP slash) for prediction of signal peptide or signal anchor of eukaryotes. Methods of both neural networks and hidden Markov models were used for prediction. Standard output format was selected.

Figure 2:
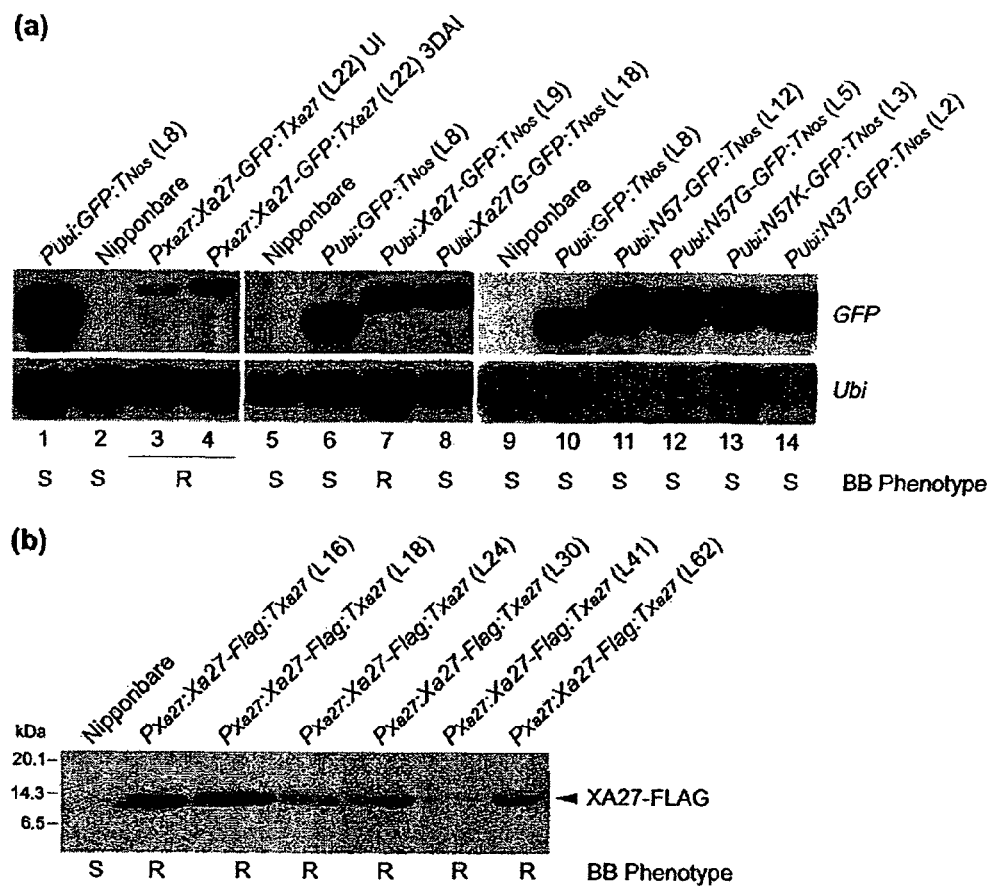

FIGS. 2a and 2b show the expression of transgenes in transgenic lines. FIG. 2a: Expression of transgenes in GFP tagging lines by RNA gel blot analysis. Lanes 1, 6 and 10, line 8 (L8) of $P_{Ubi}$:GFP:$T_{Nos}$; lanes 2, 5 and 9, Nipponbare; lanes 3 and 4, line 22 (L22) of $P_{Xa27}$:Xa27-GFP:$T_{Xa27}$ without bacterial inoculation (UI, lane 3) and at 3 days after inoculation (3 DAI) with *X. oryzae* pv. *oryzae* strain PXO99A (lane 4); lane 7, line 9 (L9) of $P_{Ubi}$:Xa27-GFP:$T_{Nos}$; lane 8, line 18 (L18) of $P_{Ubi}$:Xa27G-GFP:$T_{Nos}$; lane 11, line 12 (L12) of $P_{Ubi}$:N57-GFP:$T_{Nos}$; lane 12, line 5 (L5) of $P_{Ubi}$:N57G-GFP:$T_{Nos}$; lane 13, line 3 (L3) of $P_{Ubi}$:N57K-GFP:$T_{Nos}$; lane 14, line 2 (12) of $P_{Ubi}$:N37-GFP:$T_{Nos}$. Probe of the GFP gene (GFP) was used for gel blot hybridization. Expression of rice ubiquitin gene 2 (Ubi) was used as loading control. Disease phenotype of bacterial blight is indicated under each lane. BB, bacterial blight; R, resistant; S, susceptible. FIG. 2b: Detection of XA27-FLAG proteins in transgenic lines of $P_{Xa27}$:Xa27-FLAG:$T_{Xa27}$ by western blot analysis. Lane 1, Nipponbare; lanes 2 to 7, independent transgenic lines of $P_{Xa27}$:Xa27-FLAG:$T_{Xa27}$ at 3 days after inoculation with *X. oryze* pv. *oryzae* strain PXO99A. The size of standard protein markers (Amersham Biosciences, RPN755) is shown in kilodaltons (kDa). The position of XA27-FLAG is indicated.

FIGS. 3a-3i show that Xa27 was induced in the vascular elements by *X. oryze* pv. *oryzae*. The GFP fluorescence is shown in the green channel (FIGS. 3a, 3d and 3g). The transmission channel was taken by phase contrast 2 (Ph2) channel (FIGS. 3b, 3e and 3h). The images of the two channels are shown in merge (FIGS. 3c, 3f and 3i). m, mesophyll; p, phloem; px, protoxylem; x, xylem; xv, xylem vessel. Bar=20 µm. FIGS. 3a-3c: Leaf cross-section of Nipponbare at 3 DAI with X oryze pv. *oryzae* strain PXO99A. FIGS. 3d-3f: Leaf cross-section of un-inoculated L22 of $P_{Xa27}$:Xa27-GFP:$T_{Xa27}$. FIGS. 3g-3i: Leaf cross-section of L22 of $P_{Xa27}$:Xa27-GFP:$T_{Xa27}$ at 3 DAI with PXO99A.

Figure 3:
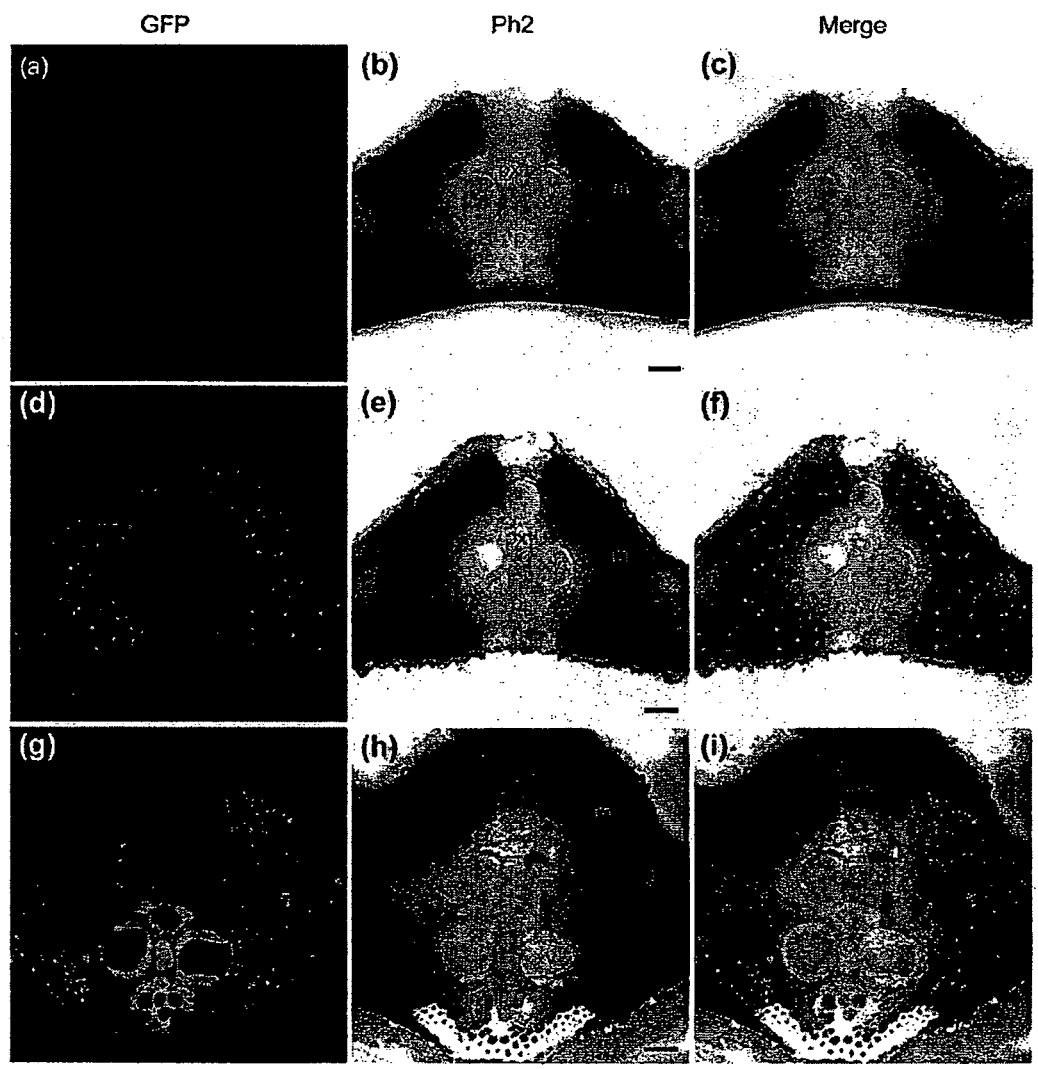
Figure 4:
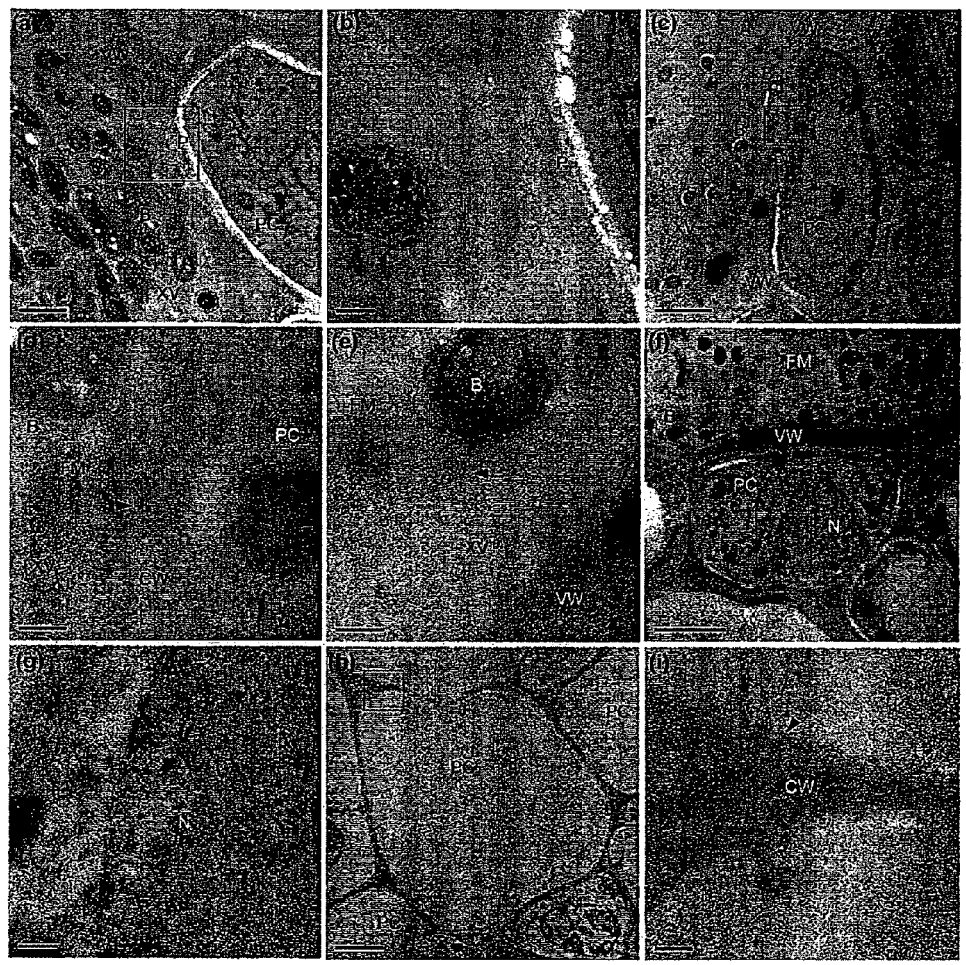

FIGS. 4a-4i show immunogold localization of Xa27-FLAG using transmission electron microscopy. Line 18 (L18) of $P_{Xa27}$:Xa27-Flag:$T_{Xa27}$ was inoculated with PXO99A and subjected to immunogold electron microscopy at 3 DAI. XA27-FLAG proteins were detected with either pre-immune serum as control (FIGS. 4a and 4b) or anti-FLAG monoclonal antibody (FIGS. 4c-4i). The immune reaction was then labeled with 10-nm (FIGS. 4a-4g) or 15-nm (FIGS. 4h and 4i) gold-conjugated goat anti-mouse IgG antibody. Gold particles are indicated by arrowheads. B, bacteria; CW, cell wall; FM, fibrillar material; N, nucleus; P, pit; PC, parenchyma cell; VW, vessel wall; XV, xylem vessel. FIG. 4a: Xylem vessel of pit area. Bar=1 µm. FIG. 4b: High magnification of the square area indicated in FIG. 4a. Bar=0.2 µm FIG. 3c: Xylem vessel, pit and parenchyma cells. Bar=2 µm. FIG. 4d: High magnification of the square area indicated in FIG. 4c. Bar=0.2 µm. FIG. 4e: Xylem vessel at high magnification. Bar=0.2 µm FIG. 4f: Xylem vessel and parenchyma cells. Bar=2 µm. FIG. 4g: High magnification of the nucleus of parenchyma cell in the square area indicated in FIG. 4f. Bar=0.2 µm. FIG. 4h: Parenchyma cells in phloem area. Bar=2 µm. FIG. 4i: High magnification of cell wall in the square area indicated in FIG. 4h. Bar=0.2 µm.

FIGS. 5a-5l show the localization of the Xa27-GFP proteins in the root cells of ectopic lines. FIGS. 5a-5c: Line 8 (L8) of $P_{Ubi}$:GFP:$T_{Nos}$ without plasmolysis. FIGS. 5d-5f: L8 of $P_{Ubi}$:GFP:$T_{Nos}$ after plasmolysis. FIGS. 5g-5i: Line 9 (L9) of $P_{Ubi}$:Xa27-GFP:$T_{Nos}$ without plasmolysis. FIGS. 5j-5l: Line 9 (L9) of $P_{Ubi}$:Xa27-GFP:$T_{Nos}$ after plasmolysis. Cell walls are indicated with arrowheads. Bar=10 µm.

Figure 5:
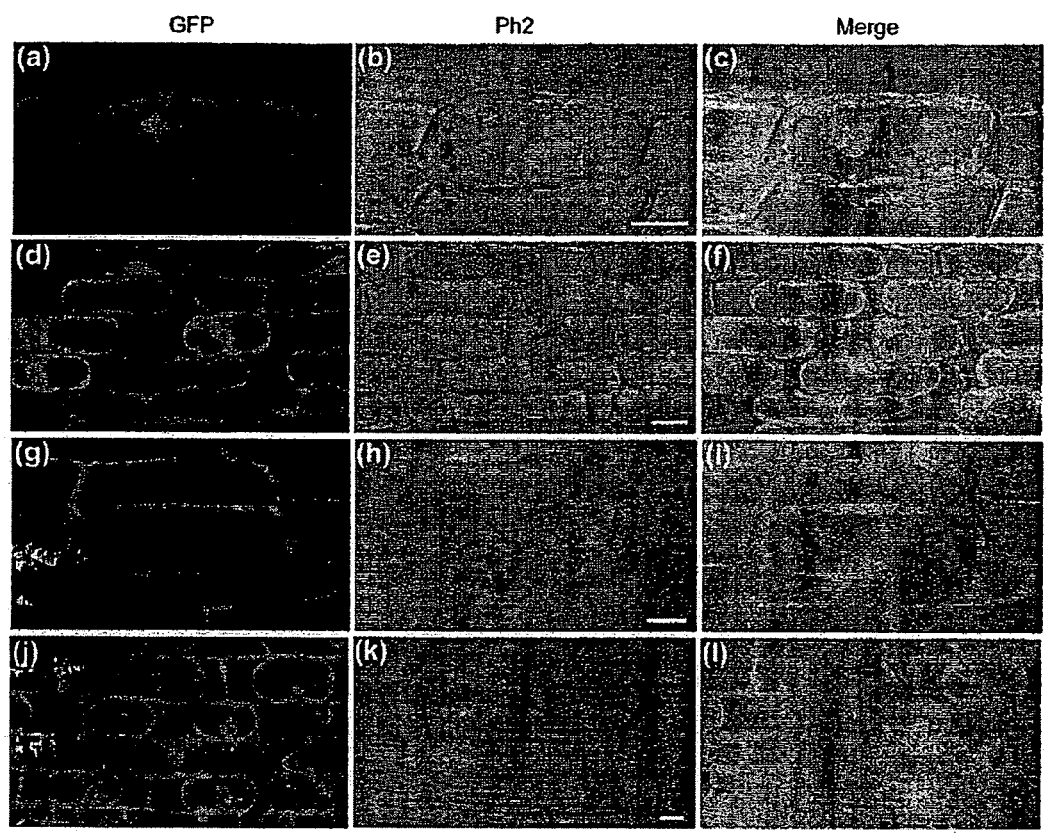
Figure 6:
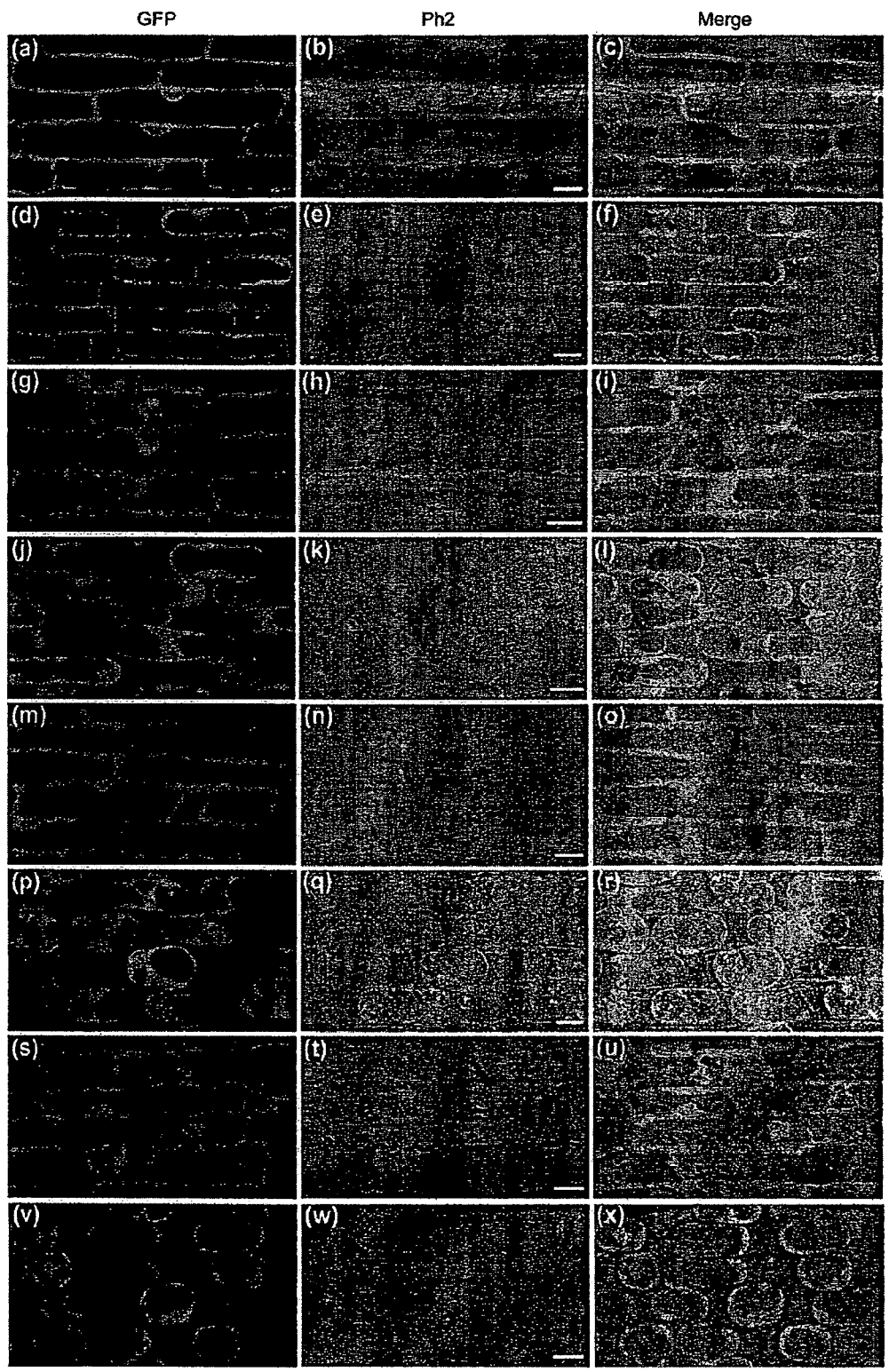

FIGS. 6a-6x show the identification and characterization of signal anchor in XA27. FIGS. 6a-6f: N-terminal 57-aa signal anchor is sufficient to localize N57-GFP to cell wall. N57-GFP shows a similar localization as that of XA27-GFP in FIGS. 5g-5l. FIGS. 6a-6c: line 12 (L12) of $P_{Ubi}$:N57-GFP:$T_{Nos}$ without plasmolysis; FIGS. 6d-6f: L12 of $P_{Ubi}$:N57-GFP:$T_{Nos}$ after plasmolysis. FIGS. 6g-6l: XA27 signal anchor without h-region failed to localize N37-GFP to cell wall. FIGS. 6g-6i: line 2 (L2) of $P_{Ubi}$:N37-GFP:$T_{Nos}$ without plasmolysis; FIGS. 6j-6l: L2 of $P_{Ubi}$:N37-GFP:$T_{Nos}$ after plasmolysis. FIGS. 6m-6r: Substitution of triple arginine residues in XA27 signal anchor with triple glycine residues failed to localize N57G-GFP to cell wall. FIGS. 6m-6o: line 5 (L5) of $P_{Ubi}$:N57G-GFP:$T_{Nos}$ without plasmolysis; FIGS. 6p-6r: line 5 (L5) of $P_{Ubi}$:N57G-GFP:$T_{Nos}$ after plasmolysis. FIGS. 6s-6x: Substitution of triple arginine residues in XA27 signal anchor with triple lysine residues failed to localize N57K-GFP to cell wall. FIGS. 6s-6u: line 3 (L3) of $P_{Ubi}$:N57K-GFP:$T_{Nos}$ without plasmolysis; FIGS. 6v-6x: L3 of $P_{Ubi}$:N57K-GFP:$T_{Nos}$ after plasmolysis. See Example 1 for mutation of XA27 signal anchor and construction of fusion genes. Cell walls are indicated with arrowheads. Bar=10 µm.

Figure 7:
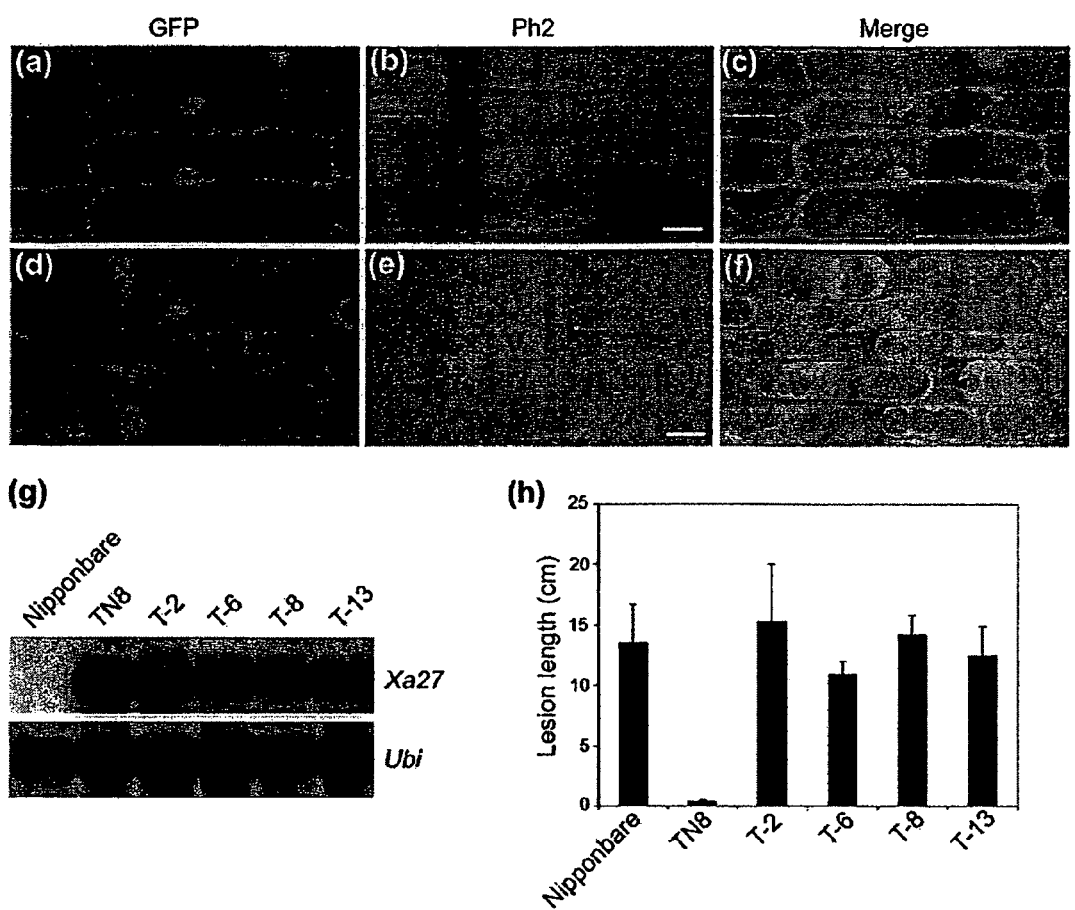

FIGS. 7a-7h show that localization of XA27 to apoplast is required for disease resistance. FIGS. 7a-7f: Substitution of triple arginine residues in XA27 signal anchor with triple glycines failed to localize XA27G-GFP to cell wall of roots in line 18 (L18) of $P_{Ubi}$:Xa27G-GFP:$T_{Nos}$. FIGS. 7a-7c: L18 of $P_{Ubi}$:Xa27G-GFP:$T_{Nos}$ without plasmolysis; FIGS. 7d-7f: L18 of $P_{Ubi}$:Xa27G-GFP:$T_{Nos}$ after plasmolysis. Cell walls are indicated with arrowheads. Bar=10 µm. FIG. 7g: Expression of transgenes in transgenic lines of $P_{Xa27}$:Xa27G:$T_{Xa27}$ and TN8 at 3 days after inoculation with *X. oryze* pv. *oryzae* strain PXO99A. Nipponbare, untransformed control; TN8, Xa27 transgenic plant (Gu et al., 2005); T-2, T-6, T-8 and T-13 are independent transgenic lines carrying the $P_{Xa27}$:Xa27G:$T_{Xa27}$ gene. FIG. 7h: Disease evaluation of transgenic $P_{Xa27}$:Xa27G:$T_{Xa27}$ lines to PXO99A. The lesion length of bacterial blight is the average values of 16 inoculated leaves with standard deviations.

DETAILED DESCRIPTION OF THE INVENTION

The present invention is directed to a functional signal anchor that localizes a fusion protein to the apoplast of vascular elements in plants. More specifically, XA27 contains an N-terminal signal anchor with triple arginine motif to localize to apoplast of vascular elements. The signal anchor is useful for engineering secretory proteins to the cell wall and/or apoplast of plant cells. The signal anchor is also useful for producing secretory proteins in transgenic plant cells in a bioreactor.

The rice gene Xa27 confers resistance to *Xanthomonas oryzae* pv. *oryzae*, the causal agent of bacterial blight in rice. However, the structural analysis of the deduced Xa27 protein (XA27) provides little or no clues as to the mode-of-action of the protein besides that a putative signal anchor is predicted at the N-terminal region of XA27. It has been discovered that XA27 depends on the signal anchor to localize to apoplast of vascular elements and this localization is indispensable for resistance to bacterial blight. Initially, the functional XA27-GFP proteins were induced and accumulated at vascular elements, especially non-live xylem vessels, where the bacterial blight pathogens multiply in the host. The localization of XA27 to apoplast of vascular elements was further verified by immunogold electron microscopy study of the functional XA27-FLAG protein and localization of XA27-GFP to cell wall of root cells in ectopic lines after plysmolysis. The 57-amino acid signal anchor of XA27 is sufficient to localize the fused GFP to cell wall. Both h-region and triple argine residues in the signal anchor are required for localization of the GFP fusion proteins to cell wall. Substitution of triple argine residues in the signal anchor with lysine residues failed in restoring the localization. Finally, de-localization of XA27 or XA27-GFP from cell wall and apoplast abolish their function for resistance to *X. oryzae* pv. *oryzae*. Thus, XA27 depends on N-terminal signal anchor to localize to apoplast of vascular elements through non-classical secretory pathway to provide non-specific resistance to *X. oryzae* pv. *oryzae*. The discovery of this function of the N-terminal signal anchor of XA27 enables protein engineering in transgenic plants or transgenic plant cells in a bioreactor.

"Encoding" or "encoded", with respect to a specified nucleic acid, means comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant mitochondria may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al., 1989). Thus, the preferred codon for a particular amino acid for a particular plant species may be derived from known gene sequences from that particular plant species.

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extension, S1 protection, and ribonuclease protection. See, e.g., *Plant Molecular Biology: A Laboratory Manual*, Clark, Ed., Springer-Verlag, Berlin (1997).

Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNNAUGG (SEQ ID NO:4), where the bolded codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous," in reference to a nucleic acid, is a nucleic acid that originates from a foreign species, or, if from the same species, is substantially modified from its native form in composition and/or genomic locus by deliberate human intervention. For example, a promoter operably linked to a heterologous nucleotide sequence can be from a species different from that from which the nucleotide sequence was derived, or, if from the same species, the promoter is not naturally found operably linked to the nucleotide sequence. A heterologous protein may originate from a foreign species, or, if from the same species, is substantially modified from its original form by deliberate human intervention.

"Host cell" means a cell which contains a vector and supports the replication and/or expression of the vector. Host cells may be prokaryotic cells such as *E. coli*, or eukaryotic cells such as yeast, insect, amphibian, or mammalian cells, excluding human cells. Preferably, host cells are monocotyledonous or dicotyledonous plant cells.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components that normally accompany or interact with it as it is found in its naturally occurring environment. The isolated material optionally comprises material not found with it in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., U.S. Pat. Nos. 5,565,350 and 6,255,113. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

As used herein, "nucleic acid" and "polynucleotide" are used interchangeably and include reference to a deoxyribonucleotide or ribonucleotide polymer, or chimeras thereof, in either single- or double-stranded form, and unless otherwise limited, encompasses known analogues having the essential nature of natural nucleotides in that they hybridize to single-stranded nucleic acids in a manner similar to naturally occurring nucleotides. A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

As used herein, "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The classes of plants which can be used in the methods of the invention include both monocotyledonous and dicotyledonous plants.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is from a plant cell. Exemplary plant promoters include, but are not limited to, those that are obtained from plants, plant viruses, and bacteria which comprise genes expressed in plant cells such as *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissues are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" or simply an "expression construct" is a nucleic acid construct, generated recombinantly or synthetically, with a series of specified nucleic acid elements which permit transcription of a particular nucleic acid in a host cell. The expression cassette can be incorporated into a plasmid, chromosome, mitochondrial DNA, plastid DNA, virus, or nucleic acid fragment. Typically, the expression cassette portion of an expression vector includes, among other sequences, a nucleic acid to be transcribed, and a promoter.

The terms "residue," "amino acid residue," and "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, 90% sequence identity, 95% or 100% sequence identity (i.e., complementary) with each other.

The term "stringent conditions" or "stringent hybridization conditions" includes reference to conditions under which a probe will selectively hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, and optionally less than 500 nucleotides in length.

Typically, stringent conditions will be those in which the salt concentration is less than about 1.5 M Na$^+$, typically about 0.01 to 1.0 M Na$^+$ concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of a destabilizing agent such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50° to 55° C. Exemplary moderate stringency conditions include hybridization in 40 to 45% formamide, 1 M NaCl, 1% SDS at 37° C., and a wash in 0.5.times. to 1×SSC at 55° to 60° C. Exemplary high stringency conditions include hybridization in 50% formamide, 1

M NaCl, 1% SDS at 37° C. for at least 4 hours, more preferably up to 12 hours or longer, and a final wash in 0.1×SSC at 60° to 65° C. for 30 minutes.

Specificity is typically a function of post-hybridization washes, the critical factors being the ionic strength and temperature of the final wash solution. For DNA-DNA hybrids, the $T_m$ (thermal melting point) can be approximated from the equation of Meinkoth and Wahl (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with .gtoreq.90% identity are sought, the $T_m$ can be decreased 10° C.

Generally, stringent conditions are selected to be about 5.degree. C. lower than the $T_m$ for the specific sequence and its complement at a defined ionic strength and pH. However, severely stringent conditions can utilize a hybridization and/or wash at 1°, 2°, 3°, or 4° C. lower than the $T_m$; moderately stringent conditions can utilize a hybridization and/or wash at 6°, 7°, 8°, 9°, or 10° C. lower than the $T_m$; low stringency conditions can utilize a hybridization and/or wash at 11°, 12°, 13°, 14°, 15°, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and Ausubel et al., 1992, *Current Protocols in Molecular Biology* (John Wiley & Sons, New York, including periodic updates).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of a heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Variants" is intended to mean substantially similar sequences. For nucleotide sequences, conservative variants include those sequences that, because of the degeneracy of the genetic code, encode the amino acid sequence of the XA27 signal anchor polypeptide of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a signal anchor polypeptide of the invention, i.e., a signal anchor that is capable of localization to the cell wall and apoplast of plant cells. Generally, variants of a particular nucleotide sequence of the invention will have at least about 50%, 60%, 65%, 70%, generally at least about 75%, 80%, 85%, 90%, 91%, 92%, 93%, 94%, 95%, 96%, 97%, 98%, 99% or more sequence identity to that particular nucleotide sequence as determined by sequence alignment programs described is U.S. Pat. No. 7,205,453 using default parameters. Characteristics of variant nucleotide sequences and protein sequences are described in U.S. Pat. No. 7,205,453. See also, U.S. Patent Application Publication No. 2006/0218670.

As used herein, "vector" includes reference to a nucleic acid used in the introduction of a polynucleotide of the present invention into a host cell. Vectors are often replicons. Expression vectors permit transcription of a nucleic acid inserted therein.

In accordance with one aspect of the present invention, a nucleic acid molecule is provided that comprises a nucleotide sequence encoding a signal anchor. In one embodiment, the signal anchor is the XA27 signal anchor having SEQ ID NO:2. In another embodiment the nucleotide sequence encoding the XA27 signal anchor has the sequence set forth in SEQ ID NO:1: In a further embodiment, the nucleotide sequence is one which incorporates the degeneracy of the genetic code. In another embodiment, the nucleotide sequence is one which has been modified to contain plant preferred codons. In one embodiment, the signal anchor is a variant of the XA27 signal anchor. In another embodiment, the variant is the XA27 signal anchor having amino acid substitutions. Guidance as to appropriate amino acid substitutions that do not affect biological activity of the protein of interest are well known in the art and may be found in the model of Dayhoff et al. (1978). Conservative substitutions, such as exchanging one amino acid with another having similar properties, may be preferred. Such conservative substitutions are well known in the art. See, U.S. Pat. No. 7,205,453. However, when it is difficult to predict the exact effect of the substitution in advance of doing so, one skilled in the art will appreciate that the effect can be evaluated by routine screening assays. Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired activity, i.e., signal anchor activity.

In accordance with another aspect of the present invention, a cassette containing the signal anchor encoding nucleotide sequence is provided. Such a cassette may be provided with a plurality of restriction sites for insertion of coding sequence of a protein of interest to be linked to the signal anchor coding sequence to create a coding sequence for a fusion protein comprising the signal anchor and the protein of interest. Alternatively, the cassette comprises a coding sequence for the signal anchor fused in proper reading frame to a coding sequence for the protein of interest to create the coding sequence for a fusion protein. The coding sequence for this fusion protein is sometimes referred to herein as a fusion gene. The cassette may also include regulatory regions operatively linked to the 5' side of the signal anchor encoding nucleotide sequence and/or to the 3' side of the restriction sites and hence to the 3' side of the inserted coding sequence for the protein of interest. A cassette containing all of these elements is also referred to herein as an expression cassette. The expression cassettes may additionally contain 5' leader sequences in the expression cassette construct. See, U.S. Pat. No. 7,205,453 and U.S. Patent Application Publication Nos. 2006/0218670 and 2006/0248616. The expression cassette may additionally contain selectable marker genes. See, U.S. Pat. No. 7,205,453 and U.S. Patent Application Publication Nos. 2006/0218670 and 2006/0248616.

In one embodiment, the expression cassette will include in the 5'-3' direction of transcription, a transcriptional initiation region (i.e., a promoter), translational initiation region, a polynucleotide encoding a signal anchor, a polynucleotide encoding a protein of interest, a translational termination region and, optionally, a transcriptional termination region functional in the host organism. The regulatory regions (i.e., promoters, transcriptional regulatory regions, and translational termination regions) and/or the polynucleotide encoding a signal anchor may be native/analogous to the host cell or to each other. Alternatively, the regulatory regions and/or the polynucleotide encoding a signal anchor may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. See, U.S. Pat. No. 7,205,453 and U.S. Patent Application Publication Nos. 2006/0218670 and 2006/0248616.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also, Guerineau et al., 1991; Proudfoot, 1991; Sanfacon et al., 1991; Mogen et al., 1990; Munroe and Jacobson, 1990; Ballas et al., 1989; and Joshi, 1987. See also, U.S. Pat. No. 7,205,453 and U.S. Patent Application Publication Nos. 2006/0218670 and 2006/0248616.

Where appropriate, the coding sequences may be optimized for increased expression in the transformed plant. That is, the coding sequences can be synthesized using plant-preferred codons for improved expression. Methods are available in the art for synthesizing plant-preferred genes. See, for example, U.S. Pat. Nos. 5,380,831, and 5,436,391, and Murray et al. (1989). See also, U.S. Pat. No. 7,205,453 and U.S. Patent Application Publication Nos. 2006/0218670 and 2006/0248616.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures. See generally, U.S. Pat. No. 7,205,453 and U.S. Patent Application Publication Nos. 2006/0218670 and 2006/0248616.

In preparing the cassette and expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved. See generally, U.S. Pat. No. 7,205,453 and U.S. Patent Application Publication Nos. 2006/0218670 and 2006/0248616.

Generally, the expression cassette will comprise a selectable marker gene for the selection of transformed cells. Selectable marker genes are utilized for the selection of transformed cells or tissues. Usually, the plant selectable marker gene will encode antibiotic resistance, with suitable genes including at least one set of genes coding for resistance to the antibiotic spectinomycin, the streptomycin phosphotransferase (spt) gene coding for streptomycin resistance, the neomycin phosphotransferase (nptII) gene encoding kanamycin or geneticin resistance, the hygromycin phosphotransferase (hpt or aphiv) gene encoding resistance to hygromycin, acetolactate synthase (als) genes. Alternatively, the plant selectable marker gene will encode herbicide resistance such as resistance to the sulfonylurea-type herbicides, glufosinate, glyphosate, ammonium, bromoxynil, imidazolinones, and 2,4-dichlorophenoxyacetate (2,4-D), including genes coding for resistance to herbicides which act to inhibit the action of glutamine synthase such as phosphinothricin or basta (e.g., the bar gene). See generally, WO 02/36782, U.S. Pat. No. 7,205,453 and U.S. Patent Application Publication No. 2006/0248616, and those references cited therein. This list of selectable marker genes is not meant to be limiting. Any selectable marker gene can be used in the present invention.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 (WO 99/48338 and U.S. Pat. No. 6,072,050); the core CaMV$^{35S}$ promoter (Odell et al., 1985); rice actin (McElroy et al., 1990); ubiquitin (Christensen and Quail, 1989 and Christensen et al., 1992); pEMU (Last et al., 1991); MAS (Velten et al., 1984); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142.

In some embodiments, it may be beneficial to express the fusion gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi (1983); Uknes et al. (1992); and Van Loon (1985). See also, U.S. Pat. No. 6,429,362 and WO 99/43819. In other embodiments, it may be beneficial to express the fusion gene from promoters include those that are expressed locally at or near the site of pathogen infection. See, for example, Marineau et al. (1987); Matton and Brisson (1989); Somssisch et al. (1986); Somssisch et al. (1988); and Yang and Klessig (1996). See also, Chen et al. (1996); Zhang and Singh (1994); Warner et al. (1993); Siebertz et al. (1989); U.S. Pat. No. 5,750,386; Cordero et al. (1992); and the references cited therein. In further embodiments, it may be beneficial to express the fusion gene from a wound-inducible promoter. Such wound-inducible promoters include potato proteinase inhibitor (pin II) gene (Ryan, 1990; Duan et al., 1996); wun1 and wun2 (U.S. Pat. No. 5,428,148); win1 and win2 (Stanford et al., 1989); systemin (McGurl et al., 1992; WIP1 (Rohmeier and Lehle, 1993); Eckelkamp et al., 1993); MPI gene (Corderok et al., 1994; and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) and McNellis et al. (1998) and tetracycline-inducible and tetracycline-repressible promoters (see, for example, Gatz et al. (1991), and U.S. Pat. Nos. 5,814,618 and 5,789,156).

In accordance with a further aspect of the present invention, transformed plants, plant cells, plant tissues and seeds thereof are additionally provided. Chimeric or transgenic plants can be generated from transformed explants, using techniques known per se. The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method, which provides for effective transformation/transfection may be employed.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al., 1986), electroporation (Riggs and Bates, 1986), *Agrobacterium*-mediated transformation (U.S. Pat. Nos. 5,563,055 and 5,981,840), direct gene transfer (Paszkowski et al., 1984), and ballistic particle acceleration (see, for example, U.S. Pat. No. 4,945,050; Tomes et al., 1995; McCabe et al., 1988). See also, Weising et al. (1988); Sanford et al. (1987) (onion); Christou et al. (1988) (soybean); McCabe et al. (1988) (soybean); Finer and McMullen (1991) (soybean); Singh et al. (1998) (soybean); Datta et al. (1990) (rice); Klein et al. (1988) (maize); Klein et al. (1988) (maize); U.S. Pat. Nos. 5,240,855; 5,322,783 and 5,324,646; Klein et al. (1988) (maize); Fromm et al. (1990) (maize); Hooykaas-Van Slogteren et al. (1984); Bytebier et al. (1987) (Liliaceae); De Wet et al. (1985) (pollen); Kaeppler et al. (1990) and Kaeppler et al. (1992) (whisker-mediated transformation); D'Halluin et al. (1992) (electroporation); Li et al. (1993) and Christou and Ford (1995) (rice); Ishida et al. (1996) (maize via *Agrobacterium tumefaciens*).

The cells that have been transformed may be grown into plants in accordance with conventional ways. See, for example, McCormick et al. (1986). These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic. One of skill will recognize that after the recombinant expression cassette is stably incorporated in transgenic plants and confirmed to be operable, it can be introduced into other plants by sexual crossing. Any of number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self-crossed to produce a homozygous inbred plant. The inbred plant produces seed containing the newly introduced heterologous nucleic acid. These seeds can be grown to produce plans that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

In one embodiment, the invention provides a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Backcrossing to a parental plant and out-crossing with a non-transgenic plant are also contemplated.

The present invention may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfae (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setara italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulchernima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesil*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

The apoplast is an excellent compartment for short-term in situ accumulation and storage of recombinant proteins. It has been shown that targeting of recombinant immunoglobulins to the apoplast significantly increased protein yields in comparison to plants where recombinant immunoglobulins were targeted to the cytosol (Conrad and Fiedler, 1998). Therefore, synthesis and assembly of fusion proteins in the plant endomembrane system and secretion using the signal anchor of the present invention may enhance the accumulation and recovery of fusion protein. In addition, targeting fusion proteins containing an insecticidal toxin protein to the apoplast can generate transgenic plants that are resistant to phloem-feeding insects.

The biochemical, technical and economic limitations on existing prokaryotic and eukaryotic expression systems have created substantial interest in developing new expression systems for the production of recombinant proteins. Like microbes, plant cells are inexpensive to grow and maintain, but because they are higher eukaryotes they can carry out many of the post-translational modifications that occur in human cells. Plant cells are also intrinsically safe, because they neither harbor human pathogens nor produce endotoxins. Thus, plants represent the most likely alternative to existing expression systems. With the availability and on going development of plant transformation techniques, most commercially important plant species can now be genetically modified to express a variety of recombinant proteins. Transgenic plants can be used in low-cost production of high quality, biologically active mammalian proteins. See, U.S. Patent Application Publication No. 2006/0248616.

Unlike field-grown plants, the performance of cultured plant cells is independent of the climate, soil quality, season, day length and weather. There is no risk of contamination with mycotoxins, herbicides or pesticides and there are fewer by-products (e.g., fibers, oils, waxes, phenolics and adventitious agents). Perhaps the most important advantage of plant cells over whole plants is the much simpler procedure for product isolation and purification especially when the product is secreted into the culture medium. For a description of plant cell bioreactors, see U.S. Patent Application Publication Nos. 2006/0248616 and 2006/0218670.

Several approaches can be used for the in vitro cultivation of plant cells, including the derivation of hairy roots, shooty teratomas, immobilized cells and suspension cell cultures. Suspension cells have the advantage that they can be cultivated relatively easily in large-scale bioreactors. Suspension cell cultures have been prepared from several different plant species, including *Arabidopsis thaliana, Taxus cuspidata, Catharanthus roseus* and important domestic crops such as tobacco, alfalfa, rice, tomato and soybean.

Plant suspension cells are prepared by the agitation of friable callus tissue in shaker flasks or fermenters to form single cells and small aggregates. Callus is undifferentiated tissue obtained by cultivating explants on solid medium containing the appropriate mixture of plant hormones to maintain the undifferentiated state. The cells are grown in liquid culture medium containing the same hormones to promote rapid growth and prevent differentiation.

If transgenic plants expressing the recombinant protein of interest are used as the source of callus tissue, further genetic manipulation is unnecessary (that is, the callus and/or suspension does not have to be selected for transformed cells). Alternatively, wild-type cell suspensions can be transformed with recombinant plasmids either by cocultivation with *Agrobacterium tumefaciens* or particle bombardment.

The principles applied to the culture of microbial cells apply also to plant cells, although cell densities and growth rates are lower. Oxygen uptake rates (and thus the oxygen transfer rates the bioreactor has to deliver) are also relatively low in plant cells. For example, Taticek et al. (1994) reported an oxygen uptake rate (OUT) of 1-3.5 mmol $l^{-1}$ $h^{-1}$ in plant cell cultures, compared with about 5-90 mmol $l^{-1}$ $h^{-1}$ in bacterial cultures. Despite these differences, conventional fermenter equipment can be modified easily to work with plant cells, and many of the fermentation strategies applied to microbial cultures can also be applied to plants.

The cells of provided methods can also be immobilized, which makes it possible to obtain a constant and prolonged production of recombinant protein. The separation of the recombinant protein and the plant biomass is also facilitated. As immobilization method, there may be mentioned immobilization in alginate or agar beads, inside polyurethane foam, or alternatively inside hollow fibers.

The cells of the provided methods can also be root cultures. The roots cultivated in vitro, in a liquid medium, are called "Hairy roots", they are roots transformed by the bacterium *Agrobacterium rhizogenes*.

Thus, there are varied methods for the recombinant expression of foreign genes in plants. It is understood that one of skill in the art would be able to use the herein provided compositions and methods to produce fusion proteins in any plant. The challenges that are associated with using different plant species, such as the transformation of a plant with a gene, or purification of the protein encoded by the gene from the plant, can be overcome using standard methods known in the art and provided herein.

The fusion proteins produced in a transgenic plant or in transgenic plant cells in culture can be isolate or purified. The term "purified recombinant heterologous protein" as used herein, is intended to refer to a recombinant heterologous protein composition, isolatable from host cells, wherein the recombinant heterologous protein is purified to any degree relative to its naturally-obtainable state, i.e., in this case, relative to its purity within a natural extract. A purified recombinant heterologous protein therefore also refers to a recombinant heterologous protein free from the environment in which it may naturally occur.

Generally, "purified" will refer to a recombinant heterologous protein composition which has been subjected to fractionation to remove various cell components. Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques.

Methods exhibiting a lower degree of relative purification may have advantages in total recovery of protein product, or in maintaining the activity of an expressed protein. Inactive products also have utility in certain embodiments, such as, e.g., in antibody generation.

Partially purified recombinant heterologous protein fractions for use in such embodiments may be obtained by subjecting a cell extract to one or a combination of the steps described above. Substituting certain steps with improved equivalents is also contemplated to be useful. For example, it is appreciated that a cation-exchange column chromatography performed utilizing an HPLC apparatus will generally result in a greater-fold purification than the same technique utilizing a low pressure chromatography system.

Thus, in accordance with the present invention, the gene of interest may encode any protein of interest that is desired to be produced in plant cells in a bioreactor. An example of such a protein is plant-based products of biopharmaceuticals, such as antibodies and edible vaccines (Fisher et al., 2004). Alternatively, the gene of interest may encode a protein of interest that is desired to be produced in the apoplast of the vascular elements. An example of such a protein is an insecticidal protein, such as lectins, ribosome inhibiting proteins, arcelins, serine protease inhibitors, cyctein protease inhibitors, α-amylase inhibitors, modified storage proteins, canatoxin-like and ureases, and Bt toxins (Carlini and Grossi-de-Sa, 2002). Other examples of proteins include those listed above.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992, *Current Protocols in Molecular Biology* (John Wiley & Sons, New York, including periodic updates); Glover, *DNA Cloning* (IRL Press, Oxford, 1985); Gelvin, *Plant Molecular Biology Manual* (Springer, 1989); Jones et al., *Plant Molecular Biology: Essential Techniques* (John Wiley & Sons, New York, 1997); Gelvin, *Plant Molecular Biology Manual*, 2nd ed (including supplement 4) (2000); Clark, *Plant Molecular Biology: A Laboratory Manual* (Springer-Verlag, Berlin (1997); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, N.Y.); Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Hogan et al., *Manipulating the Mouse Embryo*, (Cold Spring Harbor Laboratory Press, Cold Spring Harbor, N.Y., 1986); Westerfield, M., *The zebrafish book. A guide for the laboratory use of zebrafish* (Danio rerio), (4th Ed., Univ. of Oregon Press, Eugene, 2000).

EXAMPLES

The present invention is described by reference to the following Examples, which is offered by way of illustration and is not intended to limit the invention in any manner. Standard techniques well known in the art or the techniques specifically described below were utilized.

Example 1

Experimental Procedures

Constructs

The constructs used in this study are summarized in Table 1. Constructs were made based on the backbone of pC1300 or pC1305.1 and verified by DNA sequencing. Xa27-GFP fusion gene was generated by fusing GFP to C-terminal of XA27. The Xa27 coding region was amplified from NA5.2 (Gu et al., 2005) and the GFP coding region was amplified from pSSZ41 (Kolesnik et al., 2004). The fused PCR products were cloned into pC1305.1 to generate pCXa27GFP. The PstI fragment of maize ubiquitin promoter from pSSZ41 was inserted to the 5' of Xa27-GFP fusion gene in pCXa27GFP to generate pCUXa27GFP. A fragment containing partial Xa27-GFP fusion gene was amplified from pCUXa27GFP and cloned into the SacI site of NA5.2 to generate pC27Xa27GFP. The Xa27 Flag fusion gene was generated by PCR and cloned into the SpeI and SacI sites of NA5.2 to generate pC27Xa27Flag. The N57-GFP fusion gene was produced by fusing 57 amino acid residues of XA27 N-terminal region with GFP. The fusion gene was used to replace Xa27-GFP in pCUXa27GFP to generate pCUN57GFP. Similar method was used to produce pCUN37GFP, in which the 37 amino acid residues of XA27 N-terminal region were fused with GFP. The triple arginine residues (27-29) in Xa27 were mutated to triple glycine residues by PCR. The mutated Xa27 gene was used to replace wild-type Xa27 in NA5.2 to generate pC27Xa27G. The mutated Xa27 gene was also used to fuse with GFP. This Xa27G-GFP fusion gene was used to replace Xa27-GFP in pCUXa27GFP to produce pCUXa27GGFP. Similar method was used to generate constructs pCUN57GGFP and pCUN57KGFP, in which the triple arginine residues in the N57-GFP fusion gene in pCUN57GFP were mutated to triple glycine residues or triple lysine residues, respectively.

TABLE 1

Constructs Used in This Study

| Construct | Gene-of-Interest in the Construct[a] | Reference |
|---|---|---|
| NA5.2 | Wild-type Xa27 (IRBB27 allele) | Gu et al., (2005) |
| pSSZ41 | $P_{Ubi}$:GFP:$T_{Nos}$ | Kolesnik et al., (2004) |
| pCUXa27GFP | $P_{Ubi}$:Xa27-GFP:$T_{Nos}$ | This study |
| pC27Xa27GFP | $P_{Xa27}$:Xa27-GFP:$T_{Xa27}$ | This study |
| pC27Xa27Flag | $P_{Xa27}$:Xa27-Flag:$T_{Xa27}$ | This study |
| pCUN57GFP | $P_{Ubi}$:N57-GFP:$T_{Nos}$ | This study |
| pCUN37GFP | $P_{Ubi}$:N37-GFP:$T_{Nos}$ | This study |
| pCUN57GGFP | $P_{Ubi}$:N57G-GFP:$T_{Nos}$ | This study |
| pCUN57KGFP | $P_{Ubi}$:N57K-GFP:$T_{Nos}$ | This study |
| pCUXa27GGFP | $P_{Ubi}$:Xa27G-GFP:$T_{Nos}$ | This study |
| pCXa27G | $P_{Xa27}$:Xa27G:$T_{Xa27}$ | This study |

[a] $P_{Ubi}$, maize ubiquitin gene promoter; GFP, coding region of green fluorescent protein (GFP) gene (accession number AAB92477); $T_{Nos}$, terminator of nopaline synthase gene (Nos); PXa27, Xa27 promoter; Xa27-GFP, GFP fused to XA27 at C-terminal; TXa27, Xa27 terminator; Xa27-Flag, FLAG tag fused to XA27 at C-terminal; N57-GFP, GFP fused to N-terminal fifty-seven amino acid of XA27; N37-GFP, GFP fused to N-terminal thirty-seven amino acid of XA27; N57G-GFP, GFP fused to N-terminal fifty-seven amino acid of XA27 with triple argines (positions 27-29) mutated to triple glycines; N57K-GFP, GFP fused to N-terminal fifty-seven amino acid of XA27 with triple arginines mutated to triple lysines; Xa27G-GFP, GFP fused to XA27 with triple arginines mutated to triple glycines; Xa27G, XA27 mutant with triple arginine motif replaced by triple glycines.

Rice Transformation

*Agrobacterium*-mediated transformation of rice cultivar Nipponbare was carried out according to the procedures as described previously (Yin and Wang, 2000).

Molecular Analysis

DNA and RNA gel blot analysis were carried out according to the standard procedures as previously described (Sambrook et al., 1989). Rice genomic DNA was isolated from leaves as described previously (Dellaporta et al. 1983). About 2 µg DNA was used for each lane in southern analysis. Total RNA was isolated from rice leaves using RNeasy Plant Mini Kit (Qiagen, Hilden, Germany) according to manufacturer's instruction. About 20 µg total RNA was loaded in each lane for RNA gel blot analysis. The expression of rice ubiquitin gene 2 (Ubi) was used as RNA loading control. DNA probes were labeled with [$^{32}$P]-dCTP using Rediprime II random prime labeling system (Amersham Biosciences, Piscataway, N.J., USA).

Western blot was carried out with 20 µg total protein from transgenic plants and separated on 12% SDS polyacrylamide gels followed by blotting onto nitrocellulose membrane. XA27-FLAG was detected using the FLAG-M2 monoclonal antibody (Sigma, St Louis, Mo., USA) and a horseradish peroxidase-coupled secondary antibody (Bio-Rad, Hercules, Calif., USA).

Bacterial Blight Inoculation and Disease Scoring

*X. oryzae* pv. *oryzae* strains were cultured on PSA medium (10 g/L peptone, 10 g/L sucrose, 1 g/L glutamic acid, 16 g/L bacto-agar, pH 7.0) for 2-3 days at 28° C. Bacterial inocula were suspended in sterile water at an optical density of 0.5 at OD600. Bacterial blight inoculation was carried out using the leaf-clipping method (Kauffman et al., 1973). The disease symptoms were scored according to the criteria as described previously (Gu et al., 2004).

GFP Fluorescence and Plasmolysis

GFP fluorescence was examined under a ZEISS LSM510 META inverted confocal microscope (Zeiss, Jena, Germany) at 488 nm with a band pass of 505-530 nm. Transmission images were taken simultaneously by phase contrast 2 (Ph2) channel. Leaf cross sections of inoculated or uninoculated plants were sectioned manually with a No. 10 surgical blade. To induce plasmolysis in root cells, about 1 cm roots with root tips were incubated in 10% (w/v) mannitol solution for 1 h and mounted in the same solution for observation.

Immunogold Electron Microscopy

Immunogold electron microscopy was carried out according to the procedure described previously by Chye et al., (1999), with a slight modification. Leaf cross sections of about 3 mm in length from inoculated plants at 3 days after inoculation (DAI) were fixed in a solution of 0.5% glutaraldehyde and 2% paraformaldehyde in 0.1 M phosphate buffer for 4 h under vacuum. Specimens were washed with 50 mM phosphate buffer for 45 min. After dehydration in a graded ethanol series, specimens were infiltrated in LR white resin (EMS, Hatfield, Pa. 19440, USA) and embedded in gelatin capsules. Specimens were sectioned at 80 run using a Leica Ultracut microtome and mounted on Formvar-coated slotted grids. Xa27-FLAG proteins were detected with anti-FLAG monoclonal antibody (Sigma, St Louis, Mo., USA) followed by labeling with 10 or 15 nm gold conjugated goat anti-mouse IgG antibody (EMS). Mouse pre-immune serum was used to substitute anti-FLAG monoclonal antibody in control experiments. Samples on grids were further stained with 2% uranyl acetate and 1% lead citrate. Samples were visualized with a transmission electron microscope (JEOL JEM-1230, JEO LTD, Tokyo 196-8558, Japan) operating at 120 kv and photographed with a digital microphotography system (Gatan Inc., Pleasanton, Calif. 94588, USA).

Example 2

XA27 Comprises a Putative N-Terminal Signal Anchor

The Xa27 gene encodes a protein comprising 113 amino acids, however, the structural analysis of XA27 revealed little or no clues as to the mode-of-action of the protein (Gu et al., 2005). As part of the effort to characterize the biochemical function of this R protein, we investigated subcellular localization of the XA27 proteins. Interestingly, SignalP-HMM (http: slash slash www dot cbs dot dtu dot dk slash services slash SignalP slash) prediction showed that the N-terminal region of XA27 encodes a putative signal anchor (Probability=0.790) (FIG. 1). The putative signal anchor has a 37-aa n-region at the N-terminal, which comprises of positively charged residues including a triple arginine motif from residues 27 to 29, followed by a hydrophobic h-region (Emanuelsson et al, 2007). Signal anchor initiates translocation in the same way as signal peptides do, but is not cleaved by signal peptidase (von Heijne, 1988). As the rest of the polypeptide chain is translocated through the membrane, the resulting protein remains anchored to the membrane by the hydrophobic region, with a short N-terminal cytoplasmic domain (von Heijne, 1988).

Example 3

XA27 Is Induced at Vascular Elements During Bacterial Blight Infection

To investigate the localization of XA27, we generated transgenic $P_{Xa27}$:Xa27-GFP:$T_{Xa27}$ plants in Nipponbare background that lacks functional Xa27 (Table 1). The regulatory sequences in the $P_{Xa27}$:Xa27-GFP:$T_{Xa27}$ gene include 1.5-kb Xa27 promoter ($P_{Xa27}$) and 3.3-kb 3' regulation region ($T_{Xa27}$), which were cloned from the Xa27 genomic clone used in complementation study (Gu et al. 2005). Seven independent transgenic $P_{Xa27}$:Xa27-GFP:$T_{Xa27}$ lines were generated, which conferred resistance to incompatible strain PXO99$^A$ in $T_0$, $T_1$ and $T_2$ generations (data not shown). RNA gel blot analysis indicated that all of the 7 lines had weak leaking expression of the $P_{Xa27}$:Xa27-GFP:$T_{Xa27}$ gene without bacterial infection (data not shown). Line 22 (L22) of $P_{Xa27}$:Xa27-GFP:$T_{Xa27}$ that carried single copy of the transgene was selected for further analysis. The expression level of $P_{Xa27}$:Xa27-GFP:$T_{Xa27}$ in L22 was elevated after it was challenged with PXO99$^A$ (FIG. 2a, lanes 3 and 4). In uninoculated leaves of L22 plants, the leaky expressed XA27-GFP proteins were detected mainly at the mesophyll cells (FIG. 3d to f). However, after inoculation with PXO99$^A$, a large amount of XA27-GFP proteins were induced and accumulated at the vascular elements, including xylem vessels, xylem, protoxylem and phloem (FIG. 3, g to i), whereas the proteins in the mesophyll cells did not change significantly. No background GFP fluorescence was detected in leaves of non-transgenic Nipponbare plants (FIG. 3a to c).

Example 4

XA27 Localizes to Apoplast of Vascular Elements

The presence of the XA27-GFP proteins at xylem and xylem vessels, which are dead tissues, indicates that XA27 is a secretory rather than a membrane-associated or cytoplasmic protein. The XA27 proteins may have been secreted to these tissues from the neighboring parenchyma cells. To verify this assumption, we carried out immunogold assay with transgenic $P_{Xa27}$:Xa27-Flag:$T_{Xa27}$ plants (Table 1). Forty-three independent transgenic lines were generated and all showed resistance to PXO99$^A$. The Xa27-FLAG proteins induced in these resistant lines were first examined by western blot assays using anti-FLAG monoclonal antibodies. Only one uniform band of the XA27-FLAG protein with a molecular size at about 13 kDa was detected in the six resistant lines tested (FIG. 2b). Immunolocalization of the XA27-FLAG proteins was then carried out using the leaf cross-sections from line 18 (L18) at 3 days after inoculation (DAI) with PXO99$^A$. As depicted by the gold particle, the XA27-FLAG proteins localized to both interior and exterior of xylem parenchyma cells at the pit area (FIGS. 4c and d), lumen of xylem vessels (FIG. 4e) and also to secondary cell wall of parenchyma cells in the phloem (FIGS. 4h and i). In the xylem vessels, most of the XA27-FLAG proteins were found to localize in the lumen rather than associated with bacteria or vessel wall (FIG. 4e). Inside the xylem lumen, the XA27-FLAG proteins were present among fibrillar materials (FIGS. 4d to f) (Hilaire et al., 2001; Horino and Kaku, 1989), whose function is unknown. No XA27-FLAG protein was detected in the nuclei (FIGS. 4f and 4g) or other organelles of parenchyma cells of xylem in the inoculated leaves of L18 (data not shown). In control experiment, no or only background level of gold particles were labeled to the specimen when pre-immune serum was used in immunogold assay (FIGS. 4a and b).

Example 5

XA27 Localizes to Cell Wall of Roots of Ectopic Lines

To further verify the localization of XA27 to apoplast, we studied the localization of the XA27-GFP proteins in the cell wall of roots in ectopic lines for easy identification of cell wall of root cells by plasmolysis. Thirty-eight transgenic $P_{ubi}$:Xa27-GFP:$T_{Nos}$ lines were generated that carried the Xa27-GFP fusion gene under the control of maize ubiquitin gene promoter (Table 1). Among these lines, four lines carrying single copy of T-DNA insertion were selected for further studies. These lines showed high gene expression of $P_{ubi}$:Xa27-GFP:$T_{Nos}$ and were resistant to both incompatible strain PXO99$^A$ and compatible strain AXO1947 (data not shown), indicating that the XA27-GFP proteins in these ectopic lines were fully functional and provided enhanced resistance to compatible strain similar to that of the wild-type XA27 protein in ectopic lines (Gu et al., 2005). The root tips from line 9 (L9) of $P_{Ubi}$:Xa27-GFP:$T_{Nos}$ as well as from line 8 (L8) of the GFP control $P_{Ubi}$:GFP:$T_{Nos}$ (Table 1) were subjected to confocal microscopy. The GFP images of root cells of L8 indicated that the GFP proteins localized to cytoplasm and nucleus as obvious region of non-fluorescence were observed between cells (FIG. 5a to c). The XA27-GFP protein also localizes to cytoplasm (FIGS. 5g to 1). However, it may not localize to the nucleus as the nuclei were indirectly marked by a GFP halo despite clearly visible cytoplasmic GFP fluorescence (FIGS. 5g and j). In addition, XA27-GFP protein seems to localize to cell wall for no obvious gap was found between cells (FIG. 5g to i). This observation was verified by plasmolysis analysis. Upon plasmolysis, the plasma membrane withdraws and is separated from the cell wall. In L8 plants, no GFP signal was found beyond the cytoplasm of shrunken protoplasts after plasmolysis (FIGS. 5d to j). On the other hand, the XA27-GFP proteins in the L9 plants localized to cell walls as well as to the cytoplasm of shrunken protoplasts after plasmolysis (FIGS. 5j to i), which was the main difference in the subcellular localization of XA27-GFP and GFP. The localization of XA27-GFP to cell wall could not result from the ectopic expression of the $P_{ubi}$:Xa27-GFP:$T_{Nos}$ gene in L9 as its expression was comparable or less than that of the $P_{ubi}$:GFP:$T_{Nos}$ gene in L8 at both RNA and protein (based on GFP fluorescence) levels (FIG. 2a, lanes 6 and 7; FIG. 5).

Example 6

Identification and Characterization of Signal Anchor in XA27

To further verify that the putative signal anchor is present and required for XA27 localization to apoplast and cell wall for resistance to *X. oryzae* pv. *oryzae*, we cloned the predicted 57-aa signal anchor from XA27 and generated its derivatives by truncation or mutation. The putative signal anchor or its derivatives were fused with GFP and stable transgenic plants were generated to carry the fusion genes under the control of maize ubiquitin gene promoter (Table 1). The localization of the fusion proteins in root cells of transgenic lines was investigated under a confocal microscope. The $P_{Ubi}$:N57-GFP:$T_{Nos}$ gene carried the wild-type putative signal anchor fused to the N-terminal of GFP. Fifty-six individual transgenic plants were obtained from $P_{Ubi}$:N57-GFP:$T_{Nos}$. All of the transgenic plants showed high levels of transgene expression, but no disease resistance (data not shown). Line 12 (L12) of $P_{Ubi}$:N57-GFP:$T_{Nos}$ showed comparable transgene expression at RNA level to that of L8 of $P_{ubi}$:GFP:$T_{Nos}$ (FIG. 2a, lanes 10 and 11). As the XA27-GFP proteins in L9 (FIGS. 5j to 1), the N57-GFP proteins in L12 localized to cell wall in addition to cytoplasm after plasmolysis (FIG. 6d to f), which indicate that 57-aa N-terminal region of XA27 is sufficient to anchor the N57-GFP fusion proteins to cell wall.

Since the hydrophobic h-region is required for a functional signal anchor (von Heijne, 1988), we determined the h-region in the XA27 signal anchor for protein localization by truncating the h-region from the signal anchor and fusing the remaining 37-aa N-terminal region with GFP to construct $P_{Ubi}$:N37-GFP:$T_{Nos}$ (Table 1). Sixty-six independent transgenic $P_{Ubi}$:N37-GFP:$T_{Nos}$ lines were generated and all of these lines were susceptible to PXO99^A. Cells from root tips of line 2 (L2) of P$_{Ubi}$:N37-GFP:T$_{Nos}$ were subjected to confocal microscopy with and without plasmolysis. Images in FIGS. 6g to 6l clearly show that the N37-GFP fusion proteins could not localize to the cell walls any more, indicating that the h-region is essential for a functional XA27 signal anchor.

The positively charged residues in the n-region of a signal anchor are important for protein anchoring (von Heijne, 1988). The triple arginine motif in the n-region of XA27 signal anchor is conserved between XA27 and its paralogs from rice (Gu et al., 2005). To study the function of this triple arginine motif in XA27 translocation from cytosol to apoplast, we generated two signal anchor mutants and fused them with GFP. The P$_{Ubi}$:N57G-GFP:T$_{Nos}$ gene carries a mutated signal anchor by changing the triple arginine residues to triple glycine residues, whereas the P$_{Ubi}$:N57K-GFP:T$_{Nos}$ gene comprises mutation by substituting the triple arginine residues with positively charged triple lysine. Analysis with confocal microscopy and plasmolysis indicate that neither of the two fused proteins, N57G-GFP or N57K-GFP, localizes to root cell walls of ectopic lines (FIG. 6m to x). The results also suggest that the triple arginine residues, which are not replaceable by other positively charged residues such as lysines, are essential for XA27 translocation. In either of the ectopic lines that carried with truncated or mutated derivatives of the XA27 signal anchor fused to GFP, the expression of the fusion genes were comparable to those in L8 of P$_{Ubi}$:GFP:T$_{Nos}$ or L12 of P$_{Ubi}$:N57-GFP:T$_{Nos}$ (FIG. 2a lanes 10 to 14).

Example 7

Localization of XA27 to Apoplast is Required for Disease Resistance

Although XA27-GFP and Xa27-FLAG proteins were also detected in cytoplasm, the localization of these functional proteins to apoplast and cell wall may be responsible for XA27-mediated disease resistance to *X. oryzae* pv. *oryzae*. To verify this hypothesis, we mutated XA27 by replacing the triple arginine residues with triple glycine residues and generated transgenic plants containing mutated Xa27 gene (P$_{Xa27}$:Xa27G:T$_{Xa27}$) or its fusion gene with GFP (P$_{Ubi}$:Xa27G-GFP:T$_{Nos}$) (Table 1). Forty-five transgenic P$_{Ubi}$:Xa27G-GFP:T$_{Nos}$ lines were generated, however, none of these transgenic lines was resistant to PXO99^A in either T$_0$ or T$_1$ generations (data not shown). Line 18 (L18) of P$_{Ubi}$:Xa27G-GFP:T$_{Nos}$ was selected for further analysis. RNA gel blot analysis showed that expression of the P$_{Ubi}$:Xa27G-GFP:T$_{Nos}$ gene in L18 were comparable to P$_{Ubi}$:GFP:T$_{Nos}$ in L8 or P$_{Ubi}$:Xa27-GFP:T$_{Nos}$ in L9 (FIG. 2a lanes 6 to 8). However, the results from confocal microscopy and plasmolysis indicated that the XA27G-GFP proteins failed to localize to cell wall of root cells in the ectopic line (FIG. 7a to f). Similarly, mutation of the triple-arginine motif to triple glycine residues in XA27 alone abolished its disease resistance function, even though the mutated gene was driven by Xa27 native promoter. RNA gel blot analysis indicated that even though the expression of the mutated gene in the transgenic P$_{Xa27}$:Xa27G:T$_{Xa27}$ plants was comparable to that of wild-type Xa27 transgene in TN8 (Gu et al., 2005) after inoculation with PXO99^A (FIG. 7g), the P$_{Xa27}$:Xa27G:T$_{Xa27}$ plants were completely susceptible to the bacterial blight pathogen (FIG. 7h).

We have determined subcellular localization of XA27 using GFP tagging, immunogold electron microscopy, plasmolysis as well as mutagenesis. The localization of XA27-GFP to cell wall and apoplast could not have resulted from mislocalization of the fusion protein. Improperly folded GFP proteins have been reported to be secreted via a non-classical pathway, but they were non-fluorescent, (Tanudji et al., 2002). More importantly, the XA27-GFP protein is functional in providing resistance to bacterial blight which is strongly related to the localization of the fusion protein to apoplast and cell wall and depends on intact N-terminal signal anchor of XA27. The identification of signal anchor and localization of XA27 to apoplast of vascular elements facilitates further characterization of the biochemical function of the R protein.

*X. oryzae* pv. *oryzae* is a vascular pathogen and enter the rice leaf typically through hydathodes at the leaf of tip and leaf margins (Nino-Liu, 2006). Bacteria multiply in the intercellular spaces of the underlying epitheme, then enter and spread into the plant through the xylem (Nino-Liu, 2006). We also observed bacterial multiplication occurred inside the lumen of protoxylem and sieve tubes when leaf-clipping method was used for bacterial inoculation (Lifang Wu and Zhongchao Yin, unpublished data). Like other pathogenic bacteria, *X. oryzae* pv. *oryzae* does not enter the host cell. Instead, it interacts with parenchyma cells of xylem and parenchyma or companion cells of phloem when leaf-clipping method was used for bacterial inoculation. Indeed, the XA27-GFP and XA27-FLAG proteins were found to be induced in the parenchyma cells surrounding the xylem vessel, the lumen of protoxylem and the sieve tube in phloem. In incompatible interactions, bacteria in xylem vessels are enveloped by abundant fibrillar materials within 3 DAI (Hilaire et al., 2001) (FIG. 4d to f). The fibrillar materials are of host origin whose function is unknown (Horino and Kaku, 1989). It is possible that both the fibrillar materials and XA27 proteins are secreted to xylem vessels mainly through the pits between xylem vessels and parenchyma cells. The induced XA27 proteins are secreted mainly to xylem vessels, a special apoplast structure where bacteria multiply. Inside xylem vessels, the XA27-FLAG and XA27-GFP proteins were more frequently observed to be among fibrillar materials in the lumen of xylem vessels rather than attached to vessel walls. In other cells, such as parenchyma cells in the phloem or protoxylem as well as root cells of ectopic lines, the fusion proteins were more frequently observed to localize to the cell walls.

The XA27 protein has characteristics resembling extracellular PR proteins. Like other PR proteins, XA27 itself does not show resistance specificity. For instance, ectopic expression of the R protein under rice PR1 promoter provided broad-spectrum and non-specific resistance to multiple *X. oryzae* pv. *oryzae* strains including Xa27 compatible strains (Gu et al., 2005). In this study, constitutive expression of the XA27-GFP protein under maize ubiquitin promoter also conferred non-specific resistance to *X. oryzae* pv. *oryzae* strains. Most of the PR proteins are inducible proteins elicited by many environmental and developmental stimuli (Edreva, 2005). XA27 is specifically induced by AvrXa27 from incompatible pathogens. Compared with other PR proteins, the expression of XA27 is more tightly controlled and constitutive over-expression of the R protein leads to stress phenotype, such as cell wall thickening (Gu et al., 2005), growth retardation and early senescence (unpublished data). Finally, the expression of PR proteins as well as other cell wall-based extracellular defenses is likely suppressed by virulent factors from pathogens for disease development (Hauck, et al., 2003; Ott et al., 2006). In AvrXa27-Xa27 interaction, the Xa27 gene appears to deploy a mimic promoter (resistance or R promoter) that confounds the type-III effector AvrXa27, in which the virulent function has not been detected yet, and triggers the expression of the Xa27 gene. Therefore, it would be more appropriate to say that the Xa27 gene is an R promoter-driving defense gene. It remains to be determined whether Xa27 performs any signaling or antimicrobial function at biochemical level in the apoplast of vascular elements.

A type II membrane protein anchors to the membrane by its hydrophobic region in signal anchor (von Heijne 1988). However, the functional XA27-FLAG and XA27-GFP proteins are soluble in nature, and so may be the wild-type XA27. These proteins localized to apoplast and cytosol of rice cells rather than anchoring to cytoplasmic membrane or any intracellular membrane system. Therefore, although XA27 has a signal anchor, its translocation to apoplast may not follow the typical type II secretion pathway, which anchors protein to plasma membrane. In addition, the triple arginine residues in XA27 signal anchor are not replaceable by any other basic amino acid residues. Similar arginine motif was also found in the signal peptides of twin-arginine translocation (Tat) pathway (Muller and Klosgen, 2005; Robinson and bolhuis, 2004). The Tat pathway is responsible for the export of folded proteins across the cytoplasmic membrane of bacteria or thylakoid membranes of chloroplast in higher plants. Protein transported by Tat pathway possesses a cleavable signal peptide harbouring a twin-arginine concensus motif (Robinson and bolhuis, 2004). The Tat signal peptides of almost all of the substrates for the thylakoidal Tat system contain three distinct domains: N-terminal charged domain ending with twin-arginine motif, hydrophobic core domain and a more polar C-terminal domain ending with a consensus motif (Ala-X-Ala) specifying cleavage by the thylakoidal signal peptidase (Robinson and bolhuis, 2004). Although signal anchor and Tat signal peptides share some common features, Tat signal prediction with TatP 1.0 Server (http: slash slash www dot cbs dot dtu dot dk slash services slash TatP slash) failed to identify a Tat signal sequence in the N-terminal region of XA27 (data not shown). Moreover, Tat signal peptides are cleaved after protein translocation with one exception of the Rieske protein from *Paracoccus denitrificans* which depends on the uncleavable Tat signal sequence to anchor to the cytoplasmic membrane (Bachmann et al., 2006). So far, it is not known, but remains interesting to investigate, whether the XA27 protein is translocated in its folded form to apoplast of rice cells through an alternative Tat-like secretory pathway.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Axtell, M. J. and Staskawicz, B. J. (2003). Initiation of RPS2-specified disease resistance in *Arabidopsis* is coupled to the AvrRpt2-directed elimination of RIN4. *Cell* 112:369-377.

Bachmann, J. et al. (2006). The Rieske protein from *Paracoccus denitrificans* is inserted into the cytoplasmic membrane by the twin-arginine translocase. *FEBS J* 273:4817-4830.

Backus, E. A. et al. (2004). Mechanisms of hopperburn: An overview of insect taxonomy, behavior, and physiology. *Annu Rev Entomol* 50:125-151.

Ballas, N. et al. (1989). Efficient functioning of plant promoters and poly(A) sites in *Xenopus oocytes*. *Nucleic Acids Res* 17:7891-7903.

Boyes, D. C. et al. (1998). The *Arabidopsis thaliana* RPM1 disease resistance gene product is a peripheral plasma membrane protein that is degraded coincident with the hypersensitive response. *Proc Natl Acad Sci USA* 95:15849-15854.

Burch-Smith, T. M. et al. (2007). A novel role for the TIR domain in association with pathogen-derived elicitors. *PLoS Biol* 5:e68.

Bytebier, B. et al. (1987). T-DNA Organization in Tumor Cultures and Transgenic Plants of the Monocotyledon *Asparagus officinalis*. *Proc Natl Acad Sci USA* 84:5345-5349.

Canny, M. J. (1986). Transport in living plants. *Biorheology* 23:605-612.

Carlini, C. R. and Grossi-de-Sa, M. F. (2002). Plant toxic proteins with insecticidal properties. A review on their potentialities as bioinsecticides. *Toxicon* 40:1515-1539.

Chattopadhyay, A. et al. (2004). Bacterial insecticidal toxins. *Crit. Rev Microbiol* 30:33-54.

Chen, W. et al. (1996). The promoter of a H202-inducible, *Arabidopsis* glutathione S-transferase gene contains closely linked OBF- and OBP1-binding sites. *Plant J* 10:955-966.

Christensen, A. H. and Quail, P. H, (1989). Sequence analysis and transcriptional regulation by heat shock of polyubiquitin transcripts from maize. *Plant Mol Biol* 12:619-632.

Christensen, A. H. et al. (1992). Maize polyubiquitin genes: structure, thermal perturbation of expression and transcript splicing, and promoter activity following transfer to protoplasts by electroporation. *Plant Mol Biol* 18:675-689.

Christou et al. (1988). Stable Transformation of Soybean Callus by DNA-Coated Gold Particles. *Plant Physiol* 87:671-674.

Christou, P. and Ford, T. L. (1995). Recovery of chimeric rice plants from dry seed using electric discharge particle acceleration. *Annals of Botany* 75:407-413.

Christou, P. et al. (2006). Recent developments and future prospects in insect pest control in transgenic crops. *Trends Plant Sci* 11:302-308.

Chye, M. L. et al. (1999). Isolation of a gene encoding *Arabidopsis* membrane-associated acyl-CoA binding protein and immunolocalization of its gene product. *Plant J* 18:205-214.

Conrad, U. and Fiedler, U. (1998). Compartment-specific accumulation of recombinant immunoglobulins in plant cells: an essential tool for antibody production and immunomodulation of physiological functions and pathogen activity. *Plant Mol Biol* 38:101-109.

Cordero, M. J. et al. (1992). Induction of PR proteins in germinating maize seeds infected with the fungus *Fusarium moniliforme*. *Physiol Mol Plant Path* 41:189-200.

Cordero, M. J. et al. (1994). Expression of a maize proteinase inhibitor gene is induced in response to wounding and fungal infection: systemic wound-response of a monocot gene. *Plant J* 6:141-150.

Crossway, A. et al. (1986). Micromanipulation Techniques in Plant Biotechnology. *Biotechniques* 4:320-334.

Dangl, J. L. and Jones, J. D. G. (2001). Plant pathogens and integrated defense responses to infection. *Nature* 411:826-833.

Datta, S. K. et al. (1990). Genetically Engineered Fertile Indica-Rice Recovered from Protoplasts. *Biotechnology* 8:736-740.

Dayhoff et al. (1978). *Atlas of Protein Sequence and Structure*, Natl. Biomed. Res. Found. Washington, D.C.

Dellaporta, S. L. et al. (1983). A plant DNA minipreparation: version II. *Plant Mol Biol Rep* 1:19-21.

Deslandes, L. et al. (2003). Physical interaction between RRS1-R, a protein conferring resistance to bacterial wilt, and PopP2, a type III effector targeted to the plant nucleus. *Proc Natl Acad Sci USA* 100:8024-8029.

D'Halluin, K. et al. (1992). Transgenic maize plants by tissue electroporation. *Plant Cell* 4:1495-1505.

De Wet et al. (1985). in *The Experimental Manipulation of Ovule Tissues*, ed. Chapman et al. (Longman, N.Y.), pp. 197 209.

Dietz, K. J. (1997). Function and responses of the leaf apoplast under stress. *Prog Bot* 58:221-254.

Duan, X. et al. (1996). Transgenic rice plants harboring an introduced potato proteinase inhibitor II gene are insect resistant. *Nature Biotechnology* 14:494-498.

Eckelkamp, C. et al. (1993). Wound-induced systemic accumulation of a transcript coding for a Bowman-Birk trypsin inhibitor-related protein in maize (*Zea mays* L.) seedlings. *FEBS Letters* 323:73-76.

Edreva, A. (2005). Pathogenesis-related proteins: research progress in the last 15 years. *Gen Appl Plant Physiol* 31:105-124.

Emanuelsson, O. et al. (2007). Locating proteins in the cell using TargetP, SignalP and related tools. *Nature Protocols* 2:953-971.

Finer, J. J. and McMullen, M. D. (1991). Transformation of soybean via. particle bombardment of embryogenic suspension culture tissue; *In vitro Cell Dev Biol* 27P:175-182.

Fischer, R. and Emans, N. (2000). Molecular farming of pharmaceutical proteins. *Transgenic Res* 9:279-299.

Fisher, R. et al. (2004). Plant-based production of biopharmaceuticals. *Current Opinion in Plant Biology*. 7:152-158.

Flor, H. H. (1971). Current status of the gene-for-gene concept. *Annu Rev Phytopathol* 9:275-296.

Fromm, M. E. et al. (1990). Inheritance and expression of chimeric genes in the progeny of transgenic maize plants. *Biotechnology* 8:833-839.

Gatz et al. (1991). Regulation of a modified CaMV 35S promoter by the TN10-encoded Tet repressor in transgenic tobacco. *Mol Gen Genet*. 227:229-237.

Giddings, G. et al. (2000). Transgenic plants as factories for biopharmaceuticals. *Nat Biotechnol* 18:1151-1155.

Gu, K. et al. (2004). High-resolution genetic mapping of Xa27(t), a new bacterial blight resistance gene in rice, *Oryza sativa* L. *Theor Appl Genet*. 108:800-807.

Gu, K. et al. (2005). R gene expression induced by a type-III effector triggers disease resistance in rice. *Nature* 435:1122-1125.

Guerineau, F. et al. (1991). Effect of deletions in the cauliflower mosaic virus polyadenylation sequence on the choice of the polyadenylation sites in tobacco protoplasts. *Mol Gen Genet* 262:141-144.

Hammond-Kosack, K. E. and Jones, J. D. G. (1997). Plant disease resistance genes. *Annu Rev Plant Physiol Plant Mol Biol* 48:575-607.

Hauck, P. et al. (2003). A *Pseudomonas syringae* type III effector suppresses cell wall-based extracellular defense in susceptible *Arabidopsis* plants. *Proc Natl Acad Sci USA* 100:8577-8582.

He, S. Y. et al. (2004). Type III protein secretion mechanism in mammalian and plant pathogens. *Biochim Biophys Acta* 1694:181-206.

Hilaire, E. et al. (2001). Vascular defense responses in rice: peroxidase accumulation in xylem parenchyma cells and xylem wall thickening. *Mol Plant-Microbe Interact* 14:1411-1419.

Hooykaas-Van Slogteren, G. M. S. et al. (1984). Expression of Ti plasmid genes in monocotyledonous plants infected with *Agrobacterium tumefaciens*. *Nature* 311:763-764.

Horino, O. and Kaku, H. (1989). Defense mechanisms of rice against bacterial blight caused by *Xanthomonas oryzae* pv. *oryzae*. In: Bacterial blight in Rice. International Rice Research Institute, Los Banos, Philippines, pp. 135-152.

Huckelhoven, R. (2007). Cell wall-associated mechanisms of disease resistance and susceptibility. *Annu Rev Phytopathol* 45:101-127.

Ishida, Y. et al. (1996). High efficiency transformation of maize (*Zea mays* L.) mediated by *Agrobacterium tumefaciens*. *Nature Biotechnology* 14:745-750

James, E. and Lee, J. M. (2001). The production of foreign proteins from genetically modified plant cells. *Adv Biochem Eng/Biotechnol* 72:127-155.

Jia, Y. et al. (2000). Direct interaction of resistance gene and avirulence gene products confers rice blast resistance. *EMBO J.* 19:4004-4014.

Joshi, C. P. (1987). Putative polyadenylation signals in nuclear genes of higher plants: a compilation and analysis. *Nucleic Acid Res* 15:9627-9639.

Kaeppler, H. F. et al. (1990). Silicon carbide fiber-mediated DNA delivery into plant cells. *Plant Cell Reports* 9:415-418.

Kaeppler, H. F. et al. (1992). Silicon carbide fiber-mediated stable transformation of plant cells. *Theor Appl Genet* 84:560-566.

Kauffman, H. E. et al. (1973). An improved technique for evaluating resistance to rice varieties of *Xanthomonas oryzae*. *Plant Dis Rep* 57:537-541.

Kim, S. A. and Guerinot, M. L. (2007). Mining iron: iron uptake and transport in plants. *FEBS Lett* 581:2273-80.

Kim, Y. J. et al. (2002). Two distinct *Pseudomonas* effector proteins interact with the Pto kinase and activate plant immunity. *Cell* 109:589-598.

Klein, T. M. et al. (1988). Factors Influencing Gene Delivery into *Zea Mays* Cells by High-Velocity Microprojectiles. *Biotechnology* 6:559-563.

Klein, T. M. et al. (1988). Genetic transformation of maize cells by particle bombardment. *Plant Physiol* 91:440-444.

Klein, T. M. et al. (1988). Transfer of Foreign Genes into Intact Maize Cells with High-Velocity Microprojectiles. *Proc Natl Acad Sci USA* 85:4305-4309.

Kolesnik, T. et al. (2004). Establishing an efficient Ac/Ds tagging system in rice: large-scale analysis of Ds flanking sequences. *Plant J* 37:301-314.

Last, D. I. et al. (1991). pEmu: an improved promoter for gene expression in cereal cells. *Theor Appl Genet* 81:581-588.

Lauge, R. and De Wit, P. J. (1998). Fungal avirulence genes: structure and possible functions. *Fungal Genet Biol* 24:285-297.

Lee, S. W. et al. (2006). Unique characteristics of *Xanthomonas oryzae* pv. *oryzae* AvrXa21 and implications for plant innate immunity. *Proc. Natl Acad Sci USA* 103:18395-18400.

Leister, R. T. and Katagiri, F. (2000). A resistance gene product of the nucleotide binding siteleucine rich repeats class can form a complex with bacterial avirulence proteins in vivo. *Plant J* 22:345-354.

Li, L. et al. (1993). An improved rice transformation system using the biolistic method. *Plant Cell Reports* 12:250-255.

Ma, J. K.-C. et al. (2003). The production of recombinant pharmaceutical proteins in plants. *Nat Rev Genet* 4:794-805.

Marineau, C. et al. (1987). Differential accumulation of potato tuber mRNAs during the hypersensitive response induced by arachidonic acid elicitor. *Plant Mol Biol* 9:335-342.

Martin, G. B. et al. (2003). Understanding the functions of plant disease resistance proteins. *Annu Rev Plant Biol* 54:23-61.

Matton, D. P. and Brisson, N. (1989). Cloning, expression, and sequence conservation of pathogenesis-related gene transcripts of potato. *Molecular Plant-Microbe Interactions* 2:325-331.

McCabe, D. E. et al. (1988). Stable Transformation of Soybean (*Glycine Max*) by Particle Acceleration. *Biotechnology* 6:923-926.

McCormick, S. et al. (1986). Leaf disc transformation of cultivated tomato (*L. esculentum*) using *Agrobacterium tumefaciens*. *Plant Cell Reports* 5:81-84.

McElroy, D. et al. (1990). Isolation of an efficient actin promoter for use in rice transformation. *Plant Cell* 2:163-171.

McGurl, B. et al. (1992). Structure, expression, and antisense inhibition of the systemin precursor gene. *Science* 225:1570-1573.

McNellis, T. W. et al. (1998). Glucocorticoid-inducible expression of a bacterial avirulence gene in transgenic *Arabidopsis* induces hypersensitive cell death. *Plant J* 14:247-257.

Meinkoth, J. and Wahl, G. (1984). Hybridization of nucleic acids immobilized on solid supports. *Anal Biochem* 138: 267 284

Mew, T. W (1987). Current status and future prospects of research on bacterial blight of rice. *Annu Rev Phytopathol* 25:359-382.

Mogen, B. D. et al. (1990). Upstream sequences other than AAUAAA are required for efficient messenger RNA 3'-end formation in plants. *Plant Cell* 2:1261-1272.

Moran, P. J. and Thompson, G. A. (2001). Molecular responses to aphid feeding in *Arabidopsis* in relation to plant defense pathways. Plant Physiol 125:1074-1085.

Muller, M. and Klosgen, R. B. (2005). The Tat pathway in bacteria and chloroplasts. *Mol Membr Biol* 22:113-121.

Munroe, D. and Jacobson, A. et al. (1990). Tales of poly(A): a review. *Gene* 91:151-158.

Murray, E. E. et al. (1989). Codon usage in plant genes. *Nucl Acids Res* 17:477 498 (1989)

Nimchuk, Z. et al. (2000). Eukaryotic fatty acylation drives plasma membrane targeting and enhances function of several type III effector proteins from *Pseudomonas syringae*. *Cell* 101:353-363.

Nino-Liu, D. O. et al. (2006). *Xanthomonas oryzae* pathovars: model pathogens of a model crop. *Molecular Plant Pathology* 7:303-324.

Nishizawa, Y. et al. (2003). Characterization of transgenic rice plants over-expressing the stress-inducible β-glucanase gene Gns1. *Plant Mol Biol* 51:143-152.

Noctor, G. et al. (2002). Interactions between biosynthesis, compartmentation and transport in the control of glutathione homeostasis and signalling. *J Exp Bot* 53:1283-1304.

Noda, H. et al. (1991). A reovirus in the brown planthopper, *Nilaparvata lugens*. *J Gen Virol* 72:2425-2430.

Odell, J. T. et al. (1985). Identification of DNA sequences required for activity of the cauliflower mosaic virus 35S promoter. *Nature* 313:810-812.

Ott, P. G. et al. (2006). Novel extracellular chitinases rapidly and specifically induced by general bacterial elicitors and suppressed by virulent bacteria as a marker of early basal resistance in tobacco. *Mol Plant-Microbe Interact* 19:161-172.

Paszkowski, J. et al. (1984). Direct gene transfer to plants. *EMBO J* 3:2717-2722.

Pignocchi, C. and Foyer, C. H. (2003). Apoplastic ascorbate metabolism and its role in the regulation of cell signalling. *Curr Opin Plant Biol* 6:379-389.

Proudfoot, N. (1991). Poly(A) signals. *Cell* 64:671-674.

Redolfi, P. (1983). Occurrence of pathogenesis-related (b) and similar proteins in different plant species. *Neth J Plant Pathol* 89:245-254.

Reimers, P. J. et al. (1992). Increased activity of a cationic peroxidases associated with an incompatible interaction between *Xanthomonas oryzae* pv *oryzae* and rice (*Oryza sativa*). *Plant Physiol* 99:1044-1050.

Riggs, C. D. and Bates, G. W. (1986). Stable Transformation of Tobacco by Electroporation: Evidence for Plasmid Concatenation. *Proc Natl Acad Sci USA* 83:5602-5606.

Rivas, S, and Thomas, C. M. (2005). Molecular interactions between tomato and the leaf mold pathogen *Cladosporium fulvum*. *Annu Rev Phytopathol* 43:395-436.

Robinson, C. and Bolhuis, A. (2004). Tat-dependent protein targeting in prokaryotes and chloroplasts. *Biochim Biophys Acta* 1694:135-147.

Rohmeier, T. and Lehle, L. (1993). WIP1, a wound-inducible gene from maize with homology to Bowman-Birk proteinase inhibitors. *Plant Mol Biol* 22:783-792.

Ryan, C. A. (1990). Protease inhibitors in plants: genes for improving defenses against insects and pathogens. *Ann Rev Phytopath* 28:425-449.

Sambrook, J. et al. (1989). Molecular Cloning: A Laboratory Manual 2$^{nd}$ Ed., Cold Spring Harbor Cold Spring Harbor Laboratory Press.

Sanfacon, H. et al. (1991). A dissection of the cauliflower mosaic virus polyadenylation signal. *Genes Dev* 5:141-149.

Sanford, J. C. et al. (1987). Delivery of substances into cells and tissues using a particle bombardment process. *J Particulate Science and Technology* 5:27-37.

Schena, M. et al. (1991). A Steroid-Inducible Gene Expression System for Plant Cells. *Proc Natl Acad Sci USA* 88:10421-10425.

Scofield, S. R. et al. (1996). Molecular basis of gene-for-gene specificity in bacterial speck disease of tomato. *Science* 274:2063-2065.

Shen, Y. et al. (2002). The *Xanthomonas oryzae* pv. *Oryzae* raxP and raxQ genes encode an ATP sulphurylase and adenosine-5'-phosphosulphate kinase that are required for AvrXa21 avirulence activity. *Mol Microbiol* 44:37-48.

Shen, Q. H. et al. (2007). Nuclear activity of MLA immune receptors links isolate-specific and basal disease-resistance responses. *Science* 315:1098-1103.

Siebertz, B. et al. (1989). Cis-analysis of the wound-inducible promoter wun1 in transgenic tobacco plants and histochemical localization of its expression. *Plant Cell* 1:961-968.

Singh, R. J. et al. (1998). Cytological characterization of the transgenic soybean. *Theor Appl Genet* 96:319-324.

Somssisch, I. E. et al. (1986). Rapid activation by fungal elicitor of genes encoding "pathogenesis-related" proteins in cultured parsley cells. *Proc Natl Acad Sci USA* 83:2427-2430.

Somssisch, I. E. et al. (1988). Gene structure and in situ transcript localization of pathogenesis-related protein 1 in parsley. *Mol Gen Genet.* 1:93-98.

Song, W. Y. et al. (1995). A receptor kinase-like protein encoded by the rice disease resistance gene, Xa21. *Science* 270:1804-1806.

Stanford, A. et al. (1989). Differential expression within a family of novel wound-induced genes in potato. *Mol Gen Genet* 215:200-208.

Tang, X. et al. (1996). Initiation of plant disease resistance by physical interaction of AvrPto and Pto kinase. *Science* 274:2060-2063.

Tanudji, M. et al. (2002). Improperly folded green fluorescent protein is secreted via a non-classical pathway. *J Cell Sci* 115:3849-3857.

Taticek, R. A. et al. (1994). Large-scale insect and plant cell culture. *Curr Opin Biotechnol* 5:165-174.

Tomes et al. (1995). "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin).

Twyman, R. M. et al. (2003). Molecular farming in plants: host systems and expression technology. *Trends Biotechnol* 21:570-578.

Uknes, S. et al. (1992). Acquired resistance in *Arabidopsis*. *Plant Cell* 4:645-656.

Vanacker, H. et al. (1998). Pathogen-induced changes in the antioxidant status of the apoplast in barley leaves. *Plant Physiol* 117:1103-1114.

Vanacker, H. et al. (2000). Early H2O2 accumulation in mesophyll cells leads to induction of glutathione during the hyper-sensitive response in the barley-powdery mildew interaction. *Plant Physiol* 123:1289-1300.

Van Loon, L. C. (1985). Pathogenesis-related proteins. *Plant Mol Virol* 4:111-116.

Velten, J. et al. (1984). Isolation of a dual plant promoter fragment from the Ti plasmid of *Agrobacterium tumefaciens*. *EMBO J* 3:2723-2730.

Von Heijne, G. (1988). Transcending the impenetrable: how proteins come to terms with membranes. Biochim Biophys Acta 947:307-333.

Warner, S. A. et al. (1993). Isolation of an asparagus intracellular PR gene (AoPR1) wound-responsive promoter by the inverse polymerase chain reaction and its characterization in transgenic tobacco. *Plant J* 3:191-201.

Weising, K. et al. (1988). Foreign Genes in Plants: Transfer, Structure, Expression, and Applications. *Ann Rev Genet* 22:421-477.

Yang, Y. and Klessig, D. F. (1996). Isoolation and characterization of a tobacco mosaic virus-inducible myb oncogene homolog from tobacco. *Proc Natl Acad Sci USA* 93:14972-14977.

Yin Z. and Wang G. L. (2000). Evidence of multiple complex patterns of T-DNA integration into the rice genome. *Theor Appl Genet* 100:461-470.

Young, S. A. et al. (1995). Rice cationic peroxidase accumulates in xylem vessels during incompatible interactions with *Xanthomonas oryzae* pv. *oryzae*. *Plant Physiol* 107:1333-1341.

Zhang, Z. and Singh, K. B. (1994). ocs Element Promoter Sequences are Activated by Auxin and Salicylic Acid in *Arabidopsis*. *Proc Natl Acad Sci USA* 91:2507-2511.

---

What is claimed is:

1. An isolated nucleic acid molecule encoding an XA27 signal anchor peptide selected from the group consisting of (i) a peptide consisting of the amino acid sequence set forth in SEQ ID NO:2 and (ii) a variant of (i), wherein the variant has at least 90% identity to the peptide of (i) and has conservative amino acid substitutions and wherein the XA27 signal anchor peptide is effective for localizing a fusion protein having the XA27 signal anchor peptide at the N-terminus to the cell wall and/or apoplast.

2. The isolated nucleic acid molecule of claim 1 which encodes the XA27 signal anchor peptide of (i).

3. The isolated nucleic acid molecule of claim 2 consisting of the nucleotide sequence set forth in SEQ ID NO:1.

4. The isolated nucleic acid molecule of claim 2 wherein said nucleic acid comprises preferred codons of a desired plant species.

5. An isolated nucleic acid cassette comprising a first nucleic acid molecule operatively linked to a second nucleic acid molecule, wherein the first nucleic acid molecule is the nucleic acid molecule of claim 1 and the second nucleic acid molecule encodes a protein of interest, wherein the second nucleic acid molecule is heterologous to the first nucleic acid molecule and wherein the nucleic acid cassette encodes a fusion protein comprising the XA27 signal anchor peptide and the protein of interest.

6. The isolated nucleic acid cassette of claim 5 which further comprises a promoter operatively linked to the first nucleic acid molecule.

7. An isolated nucleic acid cassette comprising a first nucleic acid molecule operatively linked to a second nucleic acid molecule, wherein the first nucleic acid molecule is the nucleic acid molecule of claim 2 and the second nucleic acid molecule encodes a protein of interest, wherein the second nucleic acid molecule is heterologous to the first nucleic acid molecule and wherein the nucleic acid cassette encodes a fusion protein comprising the XA27 signal anchor peptide and the protein of interest.

8. The isolated nucleic acid cassette of claim 7 which further comprises a promoter operatively linked to the first nucleic acid molecule.

9. A process for the production of a protein of interest in a plant cell which comprises growing transgenic plants or culturing transgenic plant cells which comprise in their genome a nucleic acid cassette that encodes a fusion protein and that comprises a plant operable promoter operably linked to a first nucleic acid molecule encoding an XA27 signal anchor peptide operably linked to a second nucleic acid molecule encoding the protein of interest, wherein the second nucleic acid molecule is heterologous to the first nucleic acid molecule, wherein the XA27 signal anchor peptide is selected from the group consisting of (i) a peptide consisting of the amino acid sequence set forth in SEQ ID NO:2 and (ii) a variant of (i), wherein the variant has at least 90% identity to the peptide of (i) and has conservative amino acid substitutions and wherein the XA27 signal anchor peptide localizes the fusion protein to the cell wall and/or apoplast.

10. The method of claim 9, wherein the first nucleic acid molecule encodes the XA27 signal anchor peptide of (i).

11. The method of claim 10, wherein the first nucleic acid molecule consists of the nucleotide sequence set forth in SEQ ID NO:1.

12. The method of claim 9, wherein transgenic plants are grown.

13. The method of claim 9, wherein transgenic plant cells are cultured.

14. The method of claim 13, wherein the XA27 signal anchor peptide targets the fusion protein to the secretory pathway in the transgenic plant cells.

* * * * *